(12) United States Patent
Raycheck et al.

(10) Patent No.: US 8,211,079 B2
(45) Date of Patent: Jul. 3, 2012

(54) ANTI-POP OPEN MACROFASTENERS

(75) Inventors: Jeromy Thomas Raycheck, Lebanon, OH (US); Tracey Elaine Beckman, Mason, OH (US); Mark James Kline, Okeana, OH (US); Pablo Ibarra, Liberty Township, OH (US); Kevin Ronald Kanya, Liberty Township, OH (US); Sue Ann Mills, Cincinnati, OH (US); John Carroll Molander, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1307 days.

(21) Appl. No.: 11/240,943

(22) Filed: Sep. 30, 2005

(65) Prior Publication Data

US 2007/0078427 A1   Apr. 5, 2007

(51) Int. Cl.
*A61F 13/15* (2006.01)
(52) U.S. Cl. .................................. 604/387; 604/385.03
(58) Field of Classification Search ............. 604/385.03, 604/386–391, 358, 385.01, 385.22–385.24, 604/385.27
See application file for complete search history.

(56) References Cited

U.S. PATENT DOCUMENTS

| | | | |
|---|---|---|---|
| 3,860,003 A | 1/1975 | Buell | |
| 3,911,173 A | 10/1975 | Sprague, Jr. | |
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,673,402 A | 6/1987 | Weisman et al. | |
| 4,695,278 A | 9/1987 | Lawson | |
| 4,701,170 A | 10/1987 | Wilson et al. | |
| 4,785,996 A | 11/1988 | Ziecker et al. | |
| 4,834,735 A | 5/1989 | Alemany et al. | |
| 4,842,666 A | 6/1989 | Werenicz | |
| 4,888,231 A | 12/1989 | Angstadt | |

(Continued)

FOREIGN PATENT DOCUMENTS

GB        2 303 046 B        9/1999

(Continued)

OTHER PUBLICATIONS

International Search Report.

*Primary Examiner* — Michele M Kidwell
(74) *Attorney, Agent, or Firm* — Andrew A Paul; Laura L. Whitmer; George H. Leal

(57) ABSTRACT

A tab and slot closure system has a tab member, a slot member, and an anti-pop open device. The tab member has a tab element which has a first region and a second region. The first region includes a proximal edge, and the second region includes a distal edge. The tab element is attached to the substrate element along a line of attachment. The slot member has an inboard portion, an outboard portion, and a slot disposed between the inboard portion and the outboard portion. The anti-pop open device is disposed on either the tab member or the slot member and reduces the likelihood of the tab member unintentionally disengaging the slot member when the tab and slot closure system is fastened.

20 Claims, 15 Drawing Sheets

U.S. PATENT DOCUMENTS

| | | | |
|---|---|---|---|
| 4,892,536 | A | 1/1990 | Desmarais et al. |
| 4,909,803 | A | 3/1990 | Aziz et al. |
| 4,940,464 | A | 7/1990 | Van Gompel et al. |
| 4,968,312 | A | 11/1990 | Khan |
| 4,990,147 | A | 2/1991 | Freeland |
| 5,006,394 | A | 4/1991 | Baird |
| 5,037,416 | A | 8/1991 | Allen et al. |
| 5,062,840 | A | 11/1991 | Holt et al. |
| 5,092,861 | A | 3/1992 | Nomura et al. |
| 5,137,537 | A | 8/1992 | Herron et al. |
| 5,147,345 | A | 9/1992 | Young et al. |
| 5,151,092 | A | 9/1992 | Buell et al. |
| 5,171,236 | A | 12/1992 | Dreier et al. |
| 5,221,274 | A | 6/1993 | Buell et al. |
| 5,246,433 | A | 9/1993 | Hasse et al. |
| 5,260,345 | A | 11/1993 | Desmarais et al. |
| 5,269,775 | A | 12/1993 | Freeland et al. |
| 5,306,266 | A | 4/1994 | Freeland |
| 5,342,338 | A | 8/1994 | Roe |
| 5,387,207 | A | 2/1995 | Dyer et al. |
| 5,397,318 | A | 3/1995 | Dreier |
| 5,460,622 | A | 10/1995 | Dragoo et al. |
| 5,514,121 | A | 5/1996 | Roe et al. |
| 5,518,801 | A | 5/1996 | Chappell et al. |
| 5,540,671 | A | 7/1996 | Dreier |
| 5,554,142 | A | 9/1996 | Dreier et al. |
| 5,569,234 | A | 10/1996 | Buell et al. |
| 5,571,096 | A | 11/1996 | Dobrin et al. |
| 5,607,760 | A | 3/1997 | Roe |
| 5,609,587 | A | 3/1997 | Roe |
| 5,625,222 | A | 4/1997 | Yoneda et al. |
| 5,635,191 | A | 6/1997 | Roe et al. |
| 5,643,588 | A | 7/1997 | Roe et al. |
| 5,653,703 | A | 8/1997 | Roe et al. |
| 5,865,823 | A | 2/1999 | Curro |
| 5,897,545 | A | 4/1999 | Kline et al. |
| 5,938,648 | A | 8/1999 | Lavon et al. |
| 5,941,864 | A | 8/1999 | Roe |
| 5,957,908 | A | 9/1999 | Kline et al. |
| 5,968,025 | A | 10/1999 | Roe et al. |
| 5,977,430 | A | 11/1999 | Roe et al. |
| 5,997,520 | A | 12/1999 | Ahr et al. |
| 6,013,063 | A | 1/2000 | Roe et al. |
| 6,120,487 | A | 9/2000 | Ashton |
| 6,120,489 | A | 9/2000 | Johnson et al. |
| 6,123,695 | A | 9/2000 | Skog et al. |
| 6,168,584 | B1 | 1/2001 | Allen et al. |
| 6,432,098 | B1 | 8/2002 | Kline et al. |
| 6,648,866 | B2 | 11/2003 | Magee et al. |
| 6,680,422 | B2 | 1/2004 | Roe |
| 6,716,441 | B1 | 4/2004 | Osborne et al. |
| 6,755,809 | B2 | 6/2004 | Kline et al. |
| 6,880,211 | B2 | 4/2005 | Jackson et al. |
| 2003/0229975 | A1 | 12/2003 | Jackson et al. |
| 2003/0233082 | A1 | 12/2003 | Kline et al. |

FOREIGN PATENT DOCUMENTS

| | | |
|---|---|---|
| WO | WO 94/14395 A1 | 7/1994 |
| WO | WO 95/16746 A1 | 6/1995 |
| WO | WO 95/24173 A2 | 9/1995 |

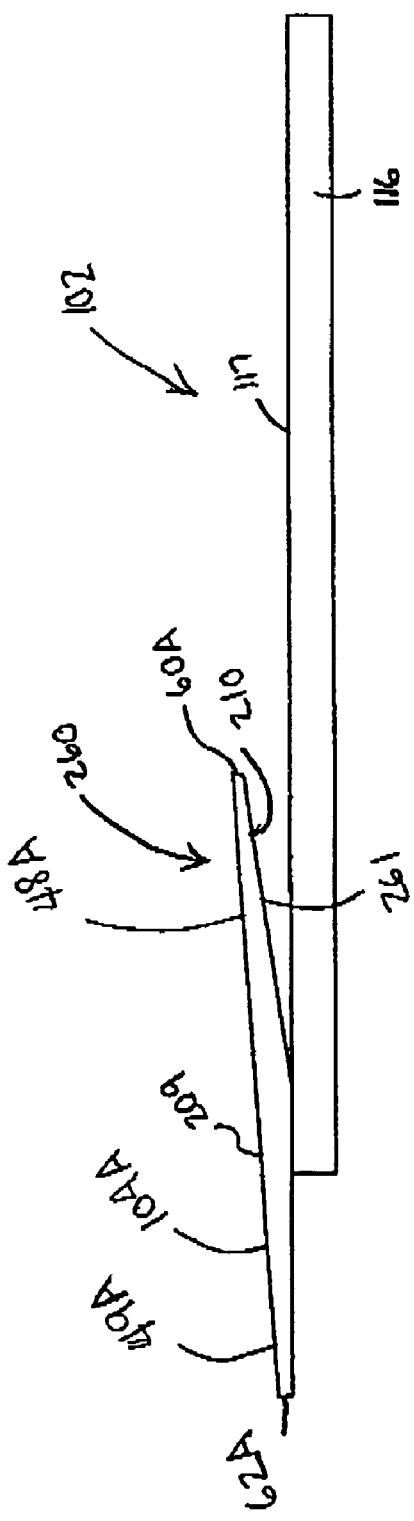
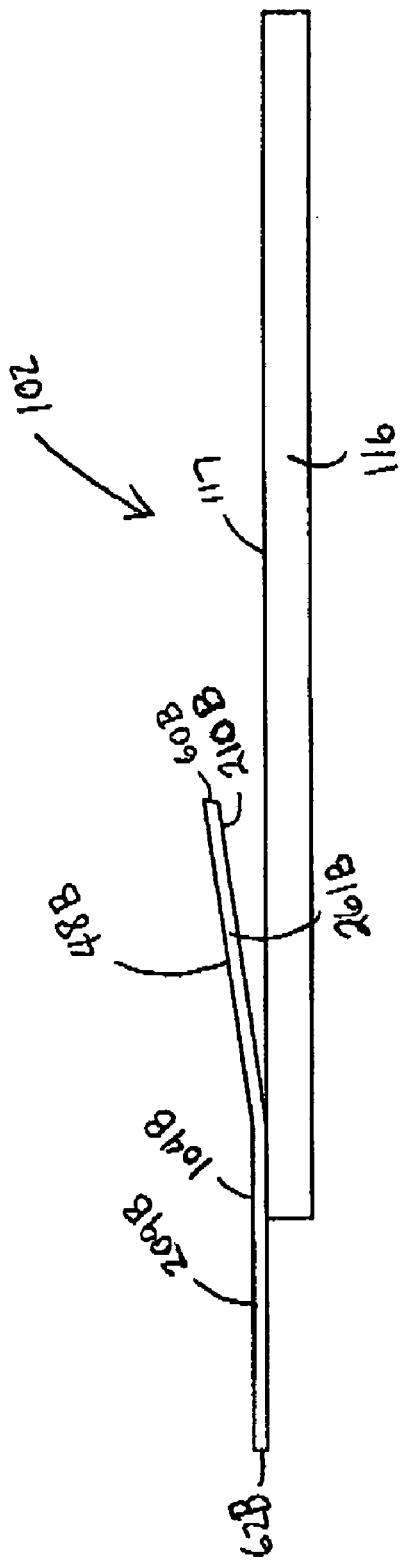
Figure 2A
Figure 2B

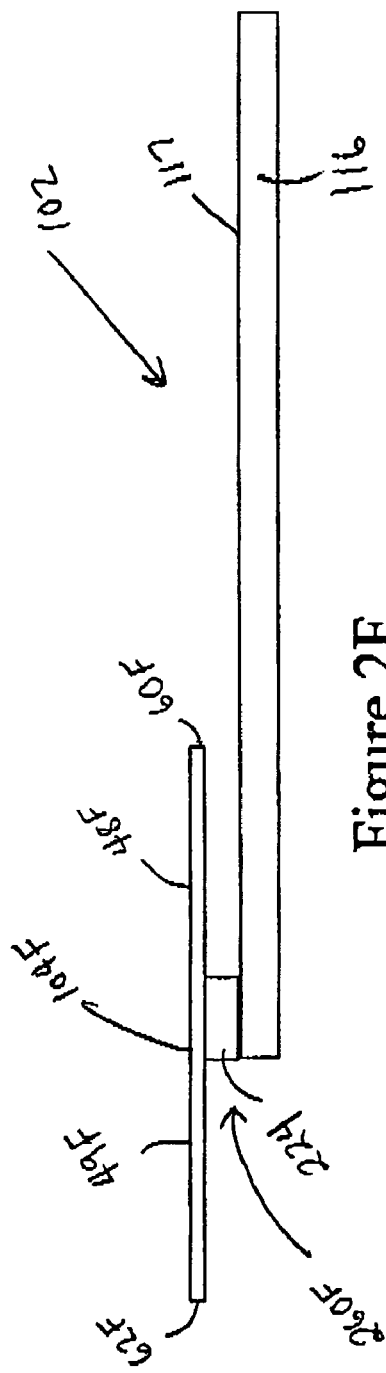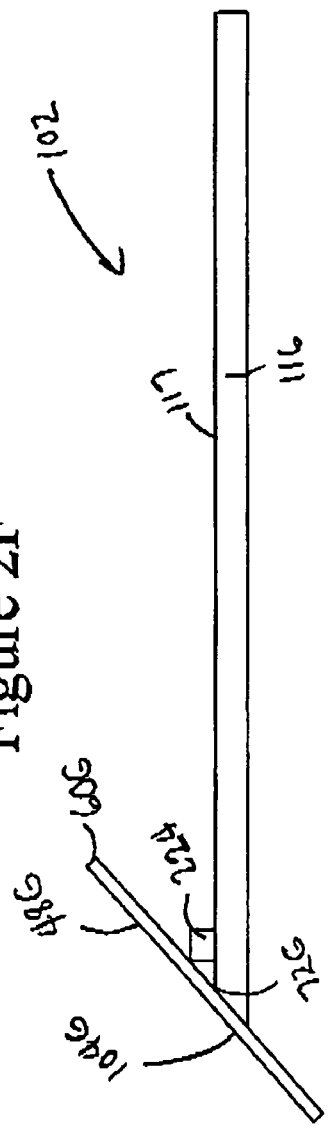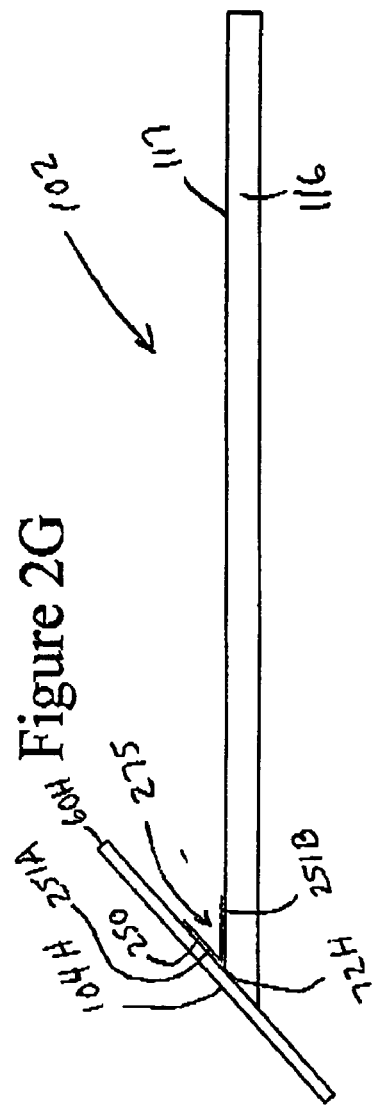
Figure 2F
Figure 2G
Figure 2H

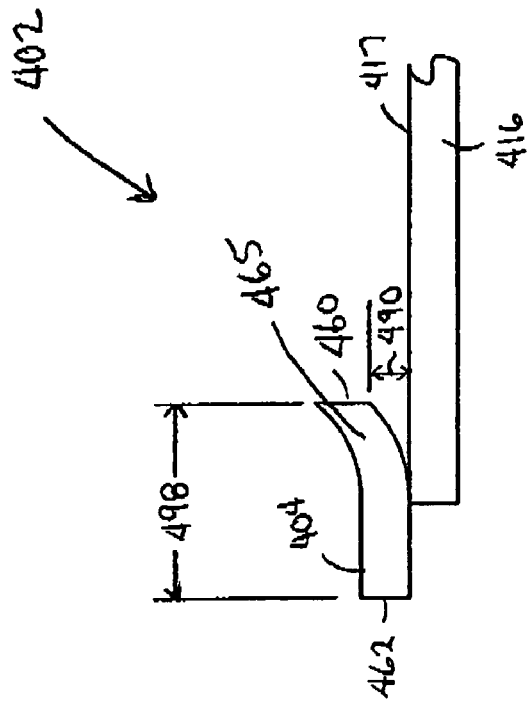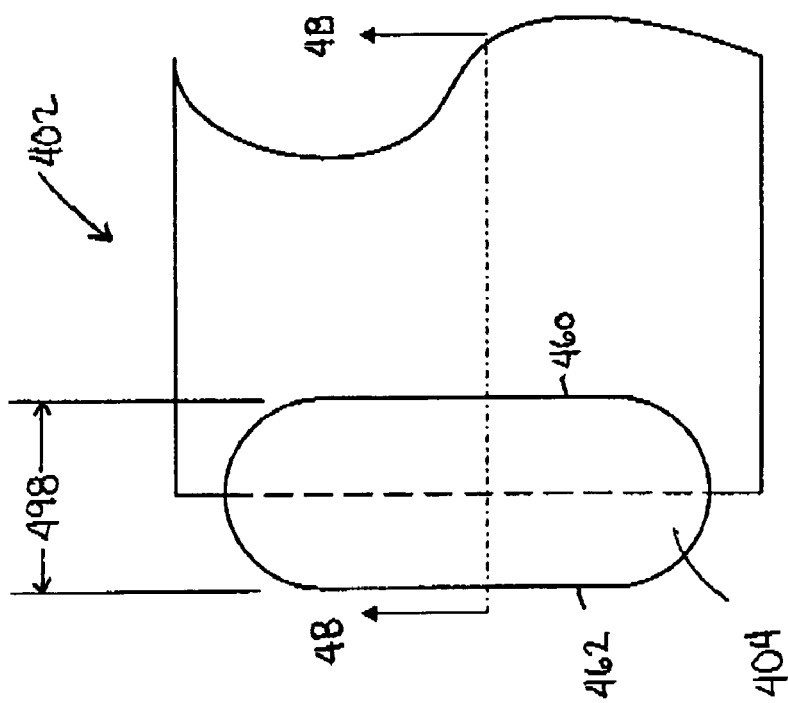
Figure 4B
Figure 4A

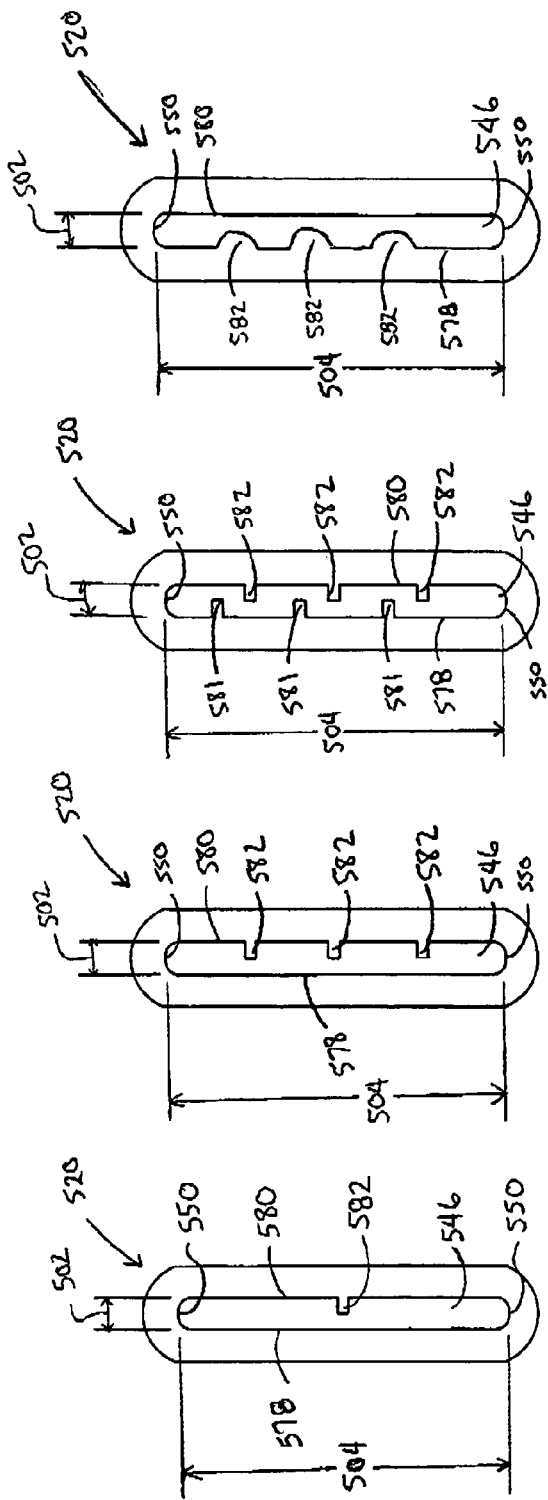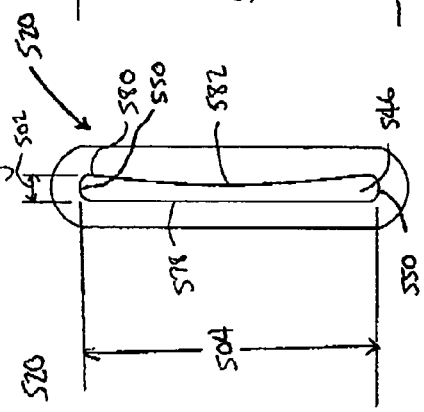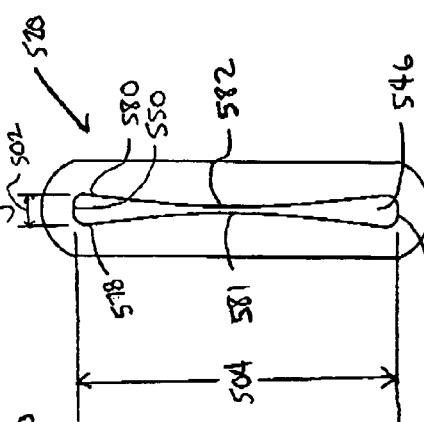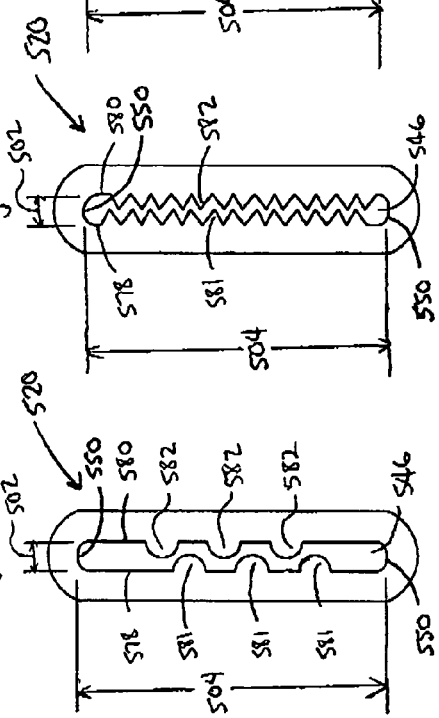

ANTI-POP OPEN MACROFASTENERS

FIELD OF THE INVENTION

The present invention pertains to tab and slot closure systems and more particularly to tab and slot closure systems having anti-pop open features. The present invention also pertains to disposable absorbent articles which utilize tab and slot closure systems as a fastening device thereon.

BACKGROUND OF THE INVENTION

Disposable absorbent articles are widely used by children and incontinent individuals. For children who are able to walk and who may be engaged in toilet training, a disposable absorbent article that has become popular is the pull-on diaper. Pull-on diapers typically include side panels which attach a front waist region to a back waist region thereby forming a waist opening and a pair of leg openings. The side panels can attach the front waist region and the back waist region via a refastenable fastening system.

One type of refastenable fastening system, which can be utilized in pull-on diapers, is a tab and slot fastening system. In general, in order to fasten the tab in the slot, a tab element is passed through the slot and is subsequently pivoted such that a portion of the tab element engages an edge of the slot to prevent the tab element from passing back through the slot. However, if the tab element does not pivot properly or is not pivoted by the caregiver or the wearer such that the portion of the tab element engages the edge of the slot, the tab element can unintentionally pass back through the slot. Generally, when a caregiver or a wearer fastens the tab and slot fastening system of a pull-on diaper, the fastening system is typically under tension. This can increase the likelihood of the tab element unintentionally passing back through the slot.

In some cases, the caregiver or wearer may not pivot the tab element to an extent necessary to prevent the tab element from passing back through the slot. For example, the caregiver or the wearer may pivot the tab element such that a portion of the tab element partially engages an edge of the slot. The partial engagement of the portion of the tab element with the edge of the slot can provide the caregiver or the wearer with a false impression that the tab and slot fastening system is fastened correctly. However, because the portion of the tab element only partially engages the edge of the slot, the tab element can still unintentionally pass back through the slot, thereby unintentionally unfastening the tab and slot fastening system. Such unintentional unfastening of the tab and slot fastening system can cause the disposable absorbent article to fall off or leak which may lead to embarrassment for the caregiver, the wearer, or both.

Consequently, there is a need for a tab and slot fastening system which reduces the likelihood of a tab element unintentionally passing back through the slot. There is also a need for a fastening system that reduces the likelihood that the tab element will pass back through the slot even without a caregiver or a wearer having to pivot the tab element after it has passed through the slot.

SUMMARY OF THE INVENTION

Tab and slot closure systems created in accordance with the present invention can reduce the likelihood of a tab element unintentionally passing back through a slot. A tab and slot closure system comprises a tab member, a slot member, and an anti-pop open device. The tab member includes a tab element and a substrate element.

The tab element has a first region and a second region. The first region includes a proximal edge, and the second region includes a distal edge. The substrate element is attached to the tab element along the line of attachment which is disposed between the distal edge and the proximal edge. The slot member has an inboard portion, an outboard portion, and a slot disposed between the inboard portion and the outboard portion.

The anti-pop open device can be disposed on the tab member or the slot member, thereby reducing the likelihood of the tab element unintentionally passing back through the slot. In a fastened state, at least a portion of the proximal edge of the tab element overlaps the outboard portion of the slot member.

In one embodiment, the tab and slot closure system may be incorporated into a disposable absorbent article for wearing about the lower torso of a wearer. The disposable absorbent article may comprise a first waist region, a second waist region, and a crotch region disposed between the first and second waist regions. A first waist edge and a second waist edge are disposed adjacent to the first waist region and the second waist region, respectively. The disposable absorbent article further comprises a first longitudinal edge and a second longitudinal edge. The disposable absorbent article includes a topsheet, a backsheet attached to at least a portion of the topsheet, and an absorbent core disposed between the topsheet and the backsheet.

The disposable absorbent article further comprises a tab and slot closure system described above; however, the anti-pop open device is disposed on the tab member. The anti-pop open device includes a beveled component which is disposed in the first region of the tab element such that a portion of the proximal edge is lifted away from the surface of the substrate element, thereby reducing the likelihood of the tab element unintentionally passing back through the slot.

In another embodiment, a plurality of disposable absorbent articles can be packaged. In this embodiment, at least one of the disposable absorbent articles includes a tab and slot closure system as described above. The tab and slot closure system includes an anti-pop open device which can be disposed on either the tab member or the slot member, thereby reducing the likelihood of the tab element unintentionally passing back through the slot.

BRIEF DESCRIPTION OF THE DRAWINGS

FIG. 2A is a cross sectional view showing a tab member of the tab and slot closure system of FIG. 1A as seen through line 2A-2A.

FIGS. 2B-2H are cross sectional views showing other embodiments of a tab member of FIG. 1A.

FIG. 4A is a plan view showing a tab member constructed in accordance with the present invention.

FIG. 4B is a cross sectional view showing the tab member of FIG. 4A as seen through the line 4B-4B.

FIGS. 5A-5I are plan views showing various slot members constructed in accordance with the present invention.

DETAILED DESCRIPTION OF THE INVENTION

Figure 1A:
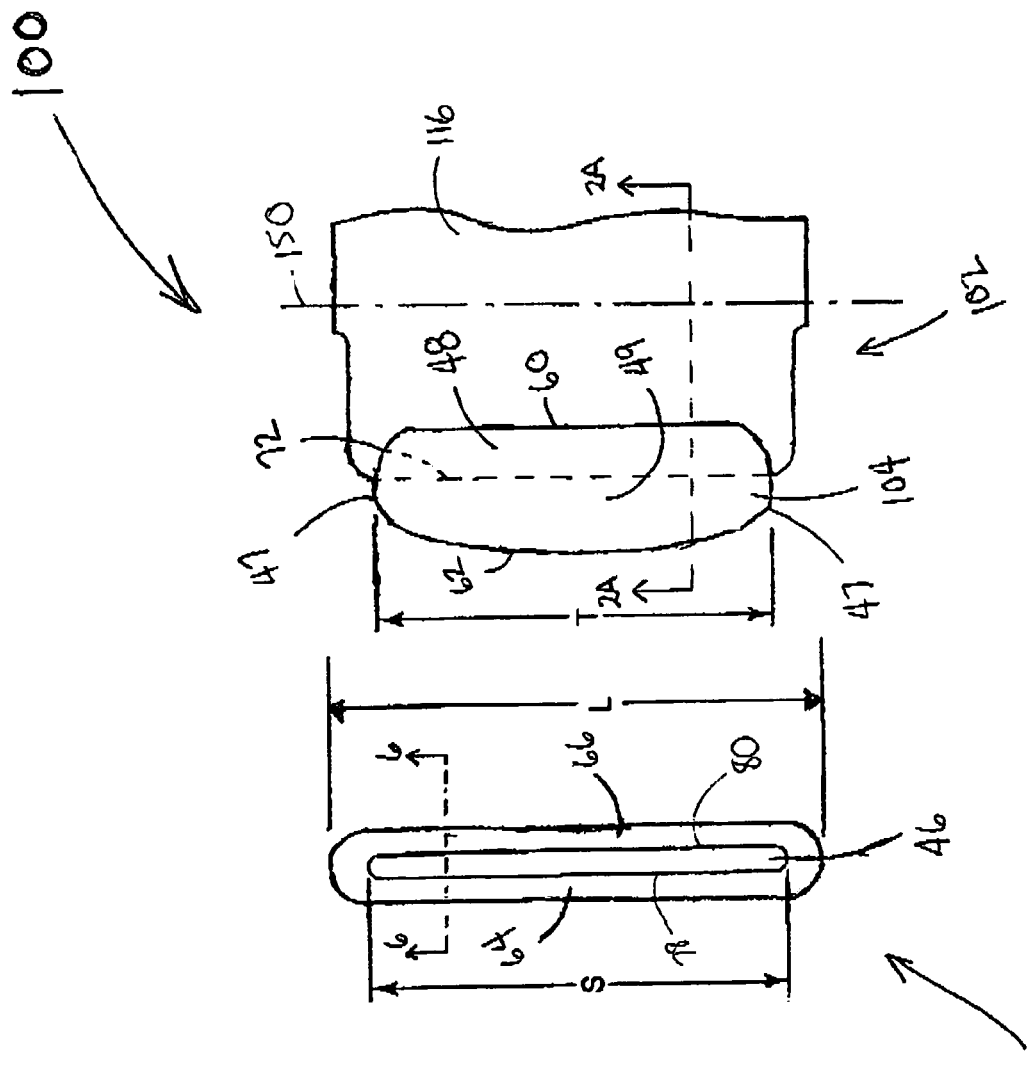
FIG. 1A is a plan view showing a tab and slot closure system constructed in accordance with the present invention.

Definitions:
As used herein, the following terms have the following meanings.

As used herein, the term "absorbent article" refers to devices that absorb and contain body exudates and, more specifically, refers to devices that are placed against or in proximity to the body of a wearer to absorb and contain the various exudates discharged from the body.

The term "attached" refers to elements being connected or united by fastening, adhering, bonding, etc. by any method suitable for the elements being fastened, secured, or joined, together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently. The term "attached" includes elements which are integrally formed with another element.

As used herein, the term "diaper" refers to an absorbent article generally worn by infants and incontinent persons about the lower torso so as to encircle the waist and legs of the wearer and that is adapted to receive and contain urinary and fecal waste. As used herein, term "diaper" also includes "pants" which is defined below.

The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner).

As used herein "elastically extensible" refers to characteristics of extensible materials that have the ability to return to approximately their original dimensions after a force that extended the extensible material is removed. Herein, any material or element described as "extensible" may also be "elastically extensible" unless otherwise provided.

The term "longitudinal" is used herein to refer to a direction which is generally parallel to the longest edge of a laminate or a substrate. If the laminate or substrate has no edge which has a longer length than other edges, then the "longitudinal" direction extends parallel to an edge, if more than one edge, or tangent to the edge, if only one edge. In the context of disposable absorbent articles, a "longitudinal" direction can run from one waist edge of a disposable absorbent article to an opposing waist edge of the disposable absorbent article and generally parallel to a line which corresponds to the maximum linear dimension of the disposable absorbent article. Directions within ±45° of the longitudinal direction are considered to be "longitudinal".

The term "lateral" refers to a direction running generally perpendicular and in the same plane as the "longitudinal" direction. In the context of disposable absorbent articles, a "lateral" direction can run from one side edge of the article to an opposing side edge of the article and generally at a right angle to the longitudinal direction and in the same plane as the longitudinal direction. Directions within ±45° of the lateral direction are considered to be "lateral".

The terms "pant", "training pant", "closed diaper", "pre-fastened diaper", and "pull-on diaper", as used herein, refer to disposable garments having a waist opening and leg openings designed for infant or adult wearers. A pant can be configured such that the pant has a closed waist and leg openings prior to being donned on the wearer, or the pant can be configured such that the waist is closed and the leg openings formed while on the wearer. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened, rear waist fastened). Examples of suitable pants are disclosed in U.S. Pat. Nos. 5,246,433; 5,569,234; 6,120,487; 6,120,489; 4,940,464; 5,092,861; 5,897,545; 5,957,908; and U.S. Patent Publication No. 2003/0233082 A1.

The term "planar" as used herein describes an element, elements, or portions thereof situated in a single plane.

The term "non-planar" as used herein describes an element, elements, or portion thereof not situated in a single plane.

Description

A tab and slot fastening system constructed in accordance with the present invention may reduce the occurrence of a tab element prematurely passing back through the slot once the fastening system is fastened. Moreover, a tab member constructed in accordance with the present invention can reduce the likelihood of the tab element prematurely passing back through the slot even when the caregiver does not partially rotate the tab after the tab has passed through the slot. Also, a slot member constructed in accordance with the present invention can reduce the likelihood of the tab element prematurely passing back through the slot after the tab and slot fastening system has been fastened. The phenomenon of the tab element prematurely passing back through the slot has been called "popping open".

As shown in FIG. 1A, a tab and slot closure system 100 constructed in accordance with the present invention may comprise a tab member 102, a slot member 120, and an anti-pop open device (not shown in FIG. 1A). The tab member 102 comprises a tab element 104 and a substrate element 116. The tab element 104 can be an elongated member having a length T, longitudinal ends 47, a first region 48, and a second region 49. The first region 48 can have a proximal edge 60 and the second region 49 can have a distal edge 62. The first region 48 comprises a portion of the tab element 104 which is not attached to the substrate element 116 to which the tab element 104 is attached. The second region 49 may comprise a portion of the tab element 104 which is attached to the substrate element 116.

As shown, the tab element 104 is attached to the substrate element 116 along a line of attachment 72 such that the first region 48 of the tab element 104 extends laterally inwardly over at least a portion of the substrate element 116. Although the line of attachment 72 is shown generally parallel to the proximal edge 60, the line of attachment 72 can also be at any angle thereto. Alternatively, the line of attachment 72 may be non-linear. For example, the line of attachment 72 may be C-shaped, D-shaped, V-shaped, or any other desired shape. The line of attachment 72 can be at an angle to a longitudinal axis 150 of the substrate element 116.

The line of attachment 72 can be disposed between the proximal edge 60 and the distal edge 62 of the first region 48 and the second region 49. Note that embodiments where the line of attachment 72 is disposed on the distal edge 62 are contemplated. Moreover, the line of attachment 72 can extend to about 25% of the length T of the tab element 104. In another embodiment, the line of attachment 72 can extend to about 50% of the length T of the tab element 104. In yet another embodiment, the line of attachment 72 can extend to about 100% of the length T of the tab element 104. In yet another embodiment, the line of attachment 72 can extend about the length T of the tab element 104 in a range from about 25% to about 100%.

The slot member 120 may comprise an inboard portion 64, an outboard portion 66, and a slot 46 disposed between the inboard portion 64 and the outboard portion 66. The inboard portion 64 may include an inboard edge 78 which can define part of the slot 46. Similarly, the outboard portion 66 may include an outboard edge 80 which can also define part of the slot 46.

The slot member 120 and the slot 46 can have lengths L and S, respectively. The length S of the slot 46 can be less than the length L of the slot member 120. The slot 46 may have any suitable length S. For example, in one embodiment, the length S of the slot 46 can be greater than or equal to the length T of the tab element 104 such that the tab element 104 is easily passed through the slot 46 without undue bending or deformation of either component. In another embodiment, the slot member 120 may include a loop under which the tab member 104 may be fed and interlocked. Loops under which tab members may be fed and interlocked are discussed in U.S. Pat. No. 6,432,089.

Figure 1B:
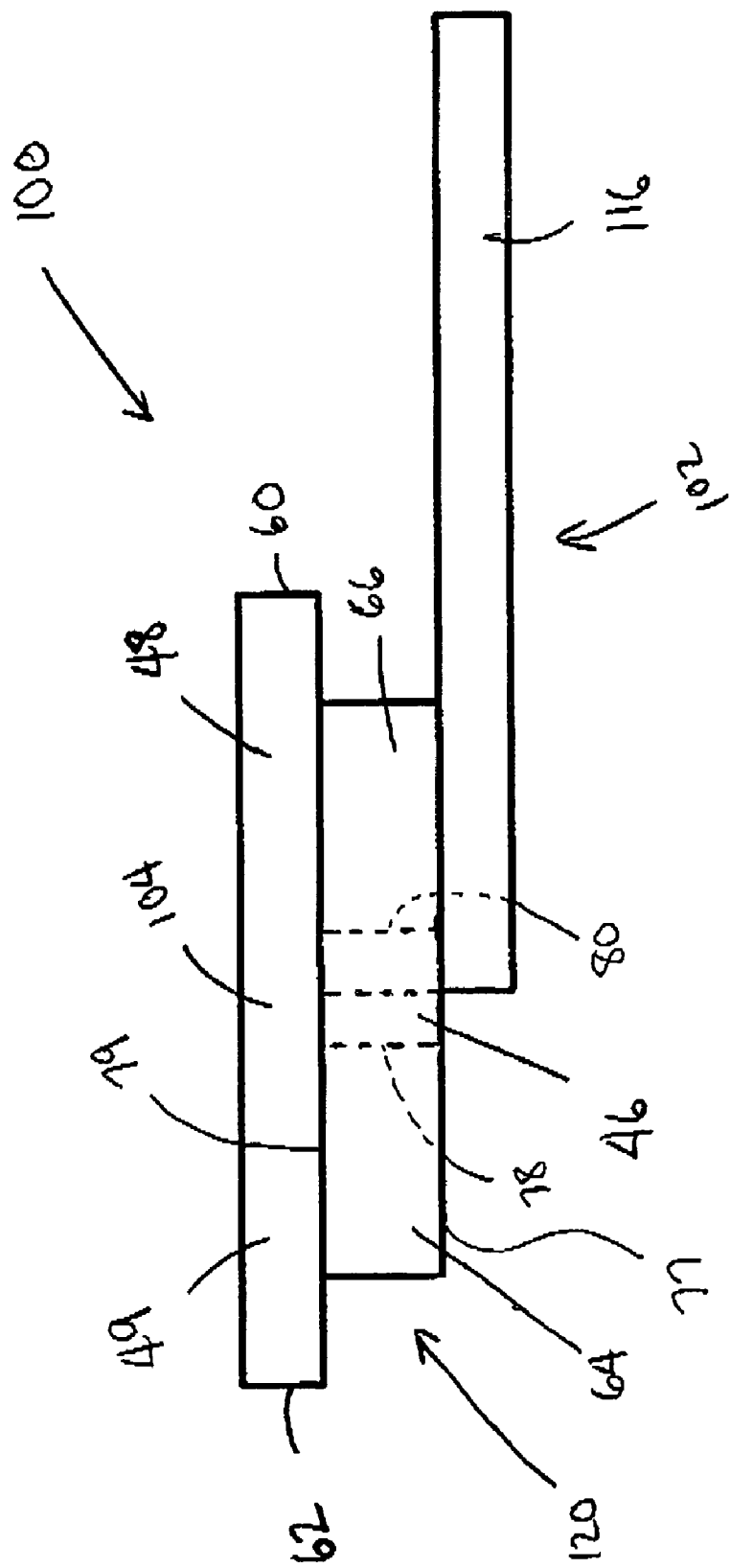
FIG. 1B is an elevation view showing the tab and slot closure system of FIG. 1A in a fastened configuration.

FIG. 1B shows the tab and slot closure system 100 in a fastened state. The tab member 102 and the slot member 120 can be fastened together by passing the tab element 104 completely through the slot 46. While the tab element 104 passes through the slot 46, the tab element 104 can be in a plane which is about parallel to a plane of the substrate element 116. An anti-pop open device (shown in FIGS. 2A-2H) can cause the proximal edge 60 to lift away from the substrate element 116. Because the proximal edge 60 is lifted away from the substrate element 116, a portion of the proximal edge 60 can more easily catch the outboard portion 66 of the slot member 120, thereby engaging the tab member 104 and the slot member 120.

The slot 46 extends from a first surface 77 through a second surface 79 of the slot member 120. In a fastened state, a portion of the first region 48 overlaps the outboard portion 66 on the second surface 79. A distance between the outboard edge 80 and the proximal edge 60 determines the amount by which the first region 48 overlaps the outboard portion 66. Similarly, a portion of the second region 49 can overlap the inboard portion 64 on the second surface 79. Also, a distance between the inboard edge 78 and the distal edge 62 determines the amount by which the second region 49 overlaps the inboard portion 64.

The first region 48 of the tab element 104 can overlap the outboard portion 66 of the slot member 120, for example, by greater than or equal to about 3 mm. As another example, the first region 48 of the tab element 104 can overlap the outboard portion 66 of the slot member 120 by greater than or equal to about 5 mm. As yet another example, the first region 48 of the tab element 104 can overlap the outboard portion 66 of the slot member 120 by greater than or equal to about 8 mm. The second region 49 can overlap the inboard portion 64 by any amount discussed above in regard to the first region 48 overlapping the outboard portion 66. The amount by which the second region 49 overlaps the inboard portion 64 does not have to be the same as the amount that the first region 48 overlaps the outboard portion 66 for any given closure system.

As previously stated, the tab and slot closure system 100 further comprises an anti-pop open device which may be disposed on either a tab member or a slot member. Regarding FIGS. 2A-2H, the anti-pop open device is shown disposed on the tab member 102. The anti-pop open device can be integrally formed in a tab element or the substrate element 116. Alternatively, the anti-pop open device may be a separate element attached to the tab member 102. When disposed on the tab member 102, the anti-pop open device can lift a portion of a proximal edge of the tab element away from a surface of the substrate element 116. Because a portion of the proximal edge is lifted away from the surface the substrate element 116, the portion of the proximal edge can more easily engage the outboard portion of the slot member without the tab element having to be pivoted by the caregiver or the wearer.

As shown in FIG. 2A, the tab member 102 may include an anti-pop open device 260 which comprises a beveled component 261 disposed in a first region 48A of a tab element 104A. The beveled component 261 can cause a portion of a proximal edge 60A of the tab element 104A to be displaced away from a surface 117 of the substrate element 116. The beveled component 261 can be disposed in the first region 48A such that a bottom surface 210 in the first region 48A is non-planar with respect to the bottom surface 210 in a second region 49A. Moreover, a top surface 209 of the tab element 104A can be planar from a distal edge 62A to a proximal edge 60A.

As shown in FIG. 2B, in another embodiment the tab member 102 may comprise a tab element 104B which comprises a beveled component 261B disposed in a first region 48B. The beveled element 261B can cause both a top surface 209B and a bottom surface 210B of the tab element 104B to be non-planar from a proximal edge 60B to a distal edge 62B.

Figure 2C:
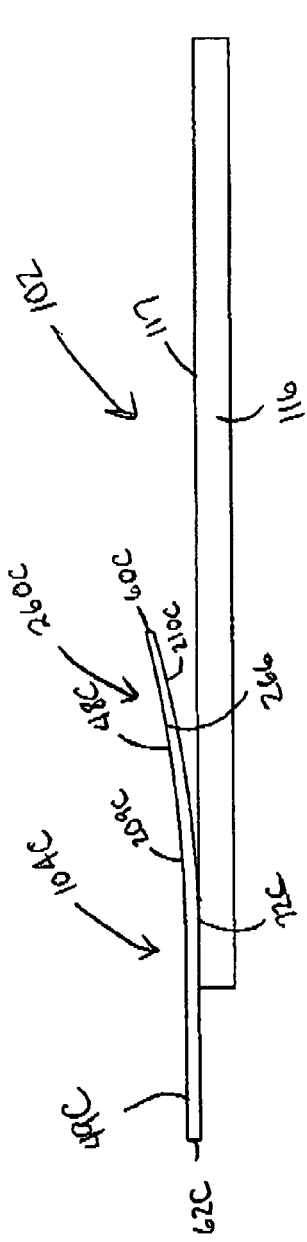

As shown in FIG. 2C, the tab member 102 may comprise a tab element 104C and an anti-pop open device 260C which includes an arcuate component 266 disposed in a first region 48C. The arcuate component 266 can cause a portion of a proximal edge 60C to be displaced from the surface 117 of the substrate element 116. The arcuate component 266 can cause both a top surface 209C and a bottom surface 210C of the tab member 104C to be non-planar from the proximal edge 60C to a line of attachment 72C. Note that a second region 49C of the tab element 104C can be generally planar in the second region 49C from the line of attachment 72C to a distal edge 62C.

Figure 2D:
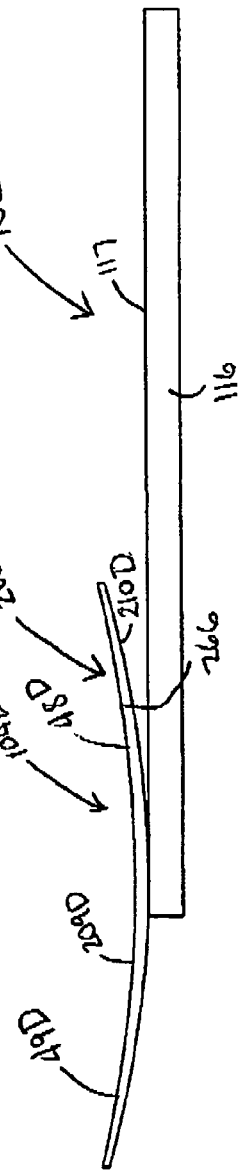

As shown in FIG. 2D, in another embodiment, the tab member 102 may comprise a tab element 104D and the anti-pop open device 260C which includes the arcuate component 266 disposed in a first region 48D. However, in addition, the tab element 104D may further comprise an arcuate component disposed in a second region 49D. The arcuate component disposed in the second region 49D can cause a bottom surface 210D and a top surface 209D of the tab element 104D to be non-planar in both the first region 48D and the second region 49D.

Figure 2E:
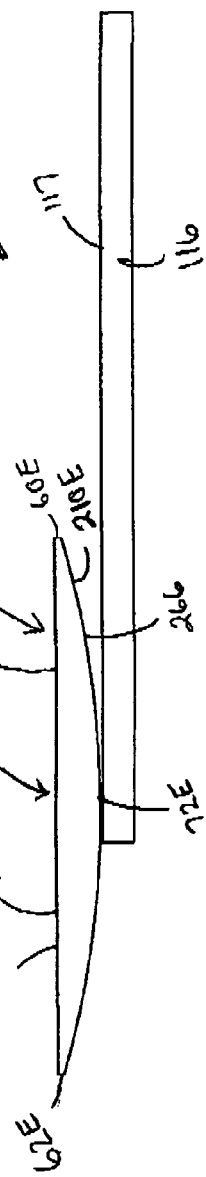

As shown in FIG. 2E, in another embodiment, the tab member 102 may comprise a tab element 104E and the anti-pop open device 260C. As shown, the anti-pop open device 260C may comprise the arcuate component 266 disposed in a first region 48E which causes a bottom surface 210E to be non-planar from a line of attachment 72E to a proximal edge 60E. In addition, the tab element 104E may further comprise an arcuate component disposed in a second region 49E which causes the bottom surface 210E of the tab member 104E to be non-planar from the line of attachment 72E to a distal edge 62E. A top surface 209E can remain planar from the distal edge 62E to the proximal edge 60E.

As shown in FIG. 2F, the tab member 102 may comprise a tab element 104F and an anti-pop open device 260F. The anti-pop open device 260F may comprise a spacing element 224 disposed between the substrate element 116 and the tab element 104F. The substrate element 116 can be attached to the spacing element 224, and the spacing element 224 can be attached to a portion of a second region 49F and/or a portion of a first region 48F of the tab element 104F. The spacing element 224 can displace the tab element 104F from the surface 117 of the substrate element 116 such that a portion of a proximal edge 60F is lifted away from the surface 117 of the substrate element 116.

The spacing element 224 can be disposed between the substrate element 116 and the tab element 104F proximate to a distal edge 62F of the tab element 104F. Alternatively, the spacing element 224 can be disposed between the substrate element 116 and the tab element 104F proximate to the proximal edge 60F of the tab element 104F (see FIG. 2G). However, the spacing element 224 should not interfere with the engagement of the proximal edge 60F with an outboard portion of a slot member.

As shown in FIG. 2G, another embodiment of the tab member 102 may comprise a tab element 104G and the spacing element 224. The spacing element 224 can be attached to the substrate element 116 and the tab element 104G in a first region 48G proximate a proximal edge 60G of the tab element 104G. The spacing element 224 can be disposed on the substrate element 116 between a line of attachment 72G and the proximal edge 60G. The spacing element 224 can be positioned between the tab element 104G and the substrate element 116, such that a portion of the proximal edge 60G is lifted away from the surface 117 of the substrate carrier 116.

As shown in FIG. 2H, in another embodiment, a tab member 102 may comprise a tab element 104H and an anti-pop open device 275. The anti-pop open device 275 may comprise a spacing element 250. The tab element 104H can be attached to the substrate element 116 at a line of attachment 72H. A first portion 251A of the spacing element 250 can be attached to the tab element 104H adjacent to the line of attachment 72H. Also, a second portion 251B of the spacing element 250 can be attached to the substrate element 116. The spacing element 250 can cause a portion of a proximal edge 60H to be lifted away from the surface 117 of the substrate element 116.

The spacing elements discussed above can be any material known in the art which can displace a portion of a proximal edge from the surface 117 of the substrate element 116. For example, the spacing element can be a nonwoven material, an elastic film, a woven material, foam, an adhesive, a laminate, paper or other cellulose product, or any combination thereof. Note that the spacing elements can be utilized in any of the embodiments discussed herein.

The spacing element can be a separate element attached to the tab member 102, a separate element attached to the tab element 104, a separate element attached to the substrate carrier 116, or a separate element attached to any combination thereof. Alternatively, the spacing element can be integrally formed in a tab element or a substrate element. For example, a spacing element may comprise a portion of a substrate element which has a thicker cross section than does another portion of the substrate element. The portion comprising a thicker cross section can be positioned such that a proximal edge is lifted away from a surface of the substrate element. In another example, a spacing element may comprise a portion of a substrate element which comprises a C-fold. In yet another example, a spacing element may comprise a portion of a substrate carrier which comprises a Z-fold.

The spacing elements may comprise discrete parts which do not extend from one longitudinal edge to another longitudinal edge of the tab element (see item 47, FIG. 1A). For example, a spacing element may comprise a plurality of discrete parts none of which fully extend from one longitudinal edge to the other longitudinal edge of the tab element. Alternatively, the spacing element may comprise a single part which extends continuously from one longitudinal edge to another longitudinal edge (see item 47, FIG. 1A) of a tab element.

Any of the embodiments discussed heretofore may utilize any combination of the anti-pop open devices described herein. For example, a tab member may comprise a spacing element and a tab element which includes an arcuate component. In another example, a tab member may comprise a plurality of spacing elements. In yet another embodiment, a tab member may comprise a spacing element and a tab element which includes a beveled component. In yet another embodiment, a tab member may comprise a tab element which includes an arcuate component and a beveled component.

The substrate element 116, of the embodiments shown in FIGS. 2A-2H, can be coextensive with a tab element. For example, the substrate element 116 in the foregoing embodiments can extend to about a line of attachment. The substrate element 116 can extend beyond the line of attachment as required. The amount that the substrate element 116 extends beyond the line of attachment can be determined in part by the load which the tab element will exert on the substrate element 116 under expected loading conditions.

The tab members discussed previously may be described as "multiplane hinge" tab members. Multiplane hinge tab members comprise two layers (or planes) of material, e.g. the tab element 104 and substrate element 116, attached in a face to face relationship along the line of attachment 72 such that at least a portion of first region 48 overhangs a portion of substrate carrier 116. The overhang of the portion of the first region results in a bottom surface of the tab element in the first region being in a face to face relationship with the surface 117 of the substrate element 116.

The process of attaching a tab element to a substrate element typically requires subjecting the attached tab element and substrate element to pressures which ensure bonding between the tab element and the substrate element. So, in contrast to the present invention, conventional multiplane hinged tab members without an anti-pop open device may be particularly susceptible to pop-open failures because the application of pressure can make a portion of a proximal edge of the tab element less likely to lift away from a surface of the substrate element, thereby increasing the likelihood of the tab element popping out of the slot member.

Figure 3B:
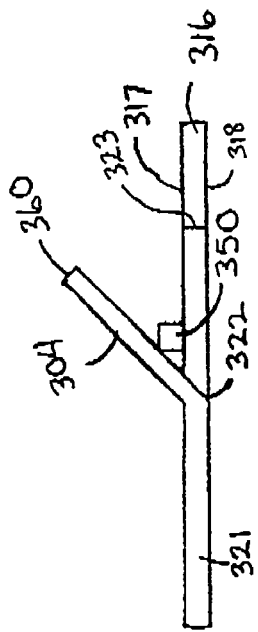
FIG. 3B is a cross sectional view showing the tab member of FIG. 3A as seen through line 3B-3B.
Figure 3A:
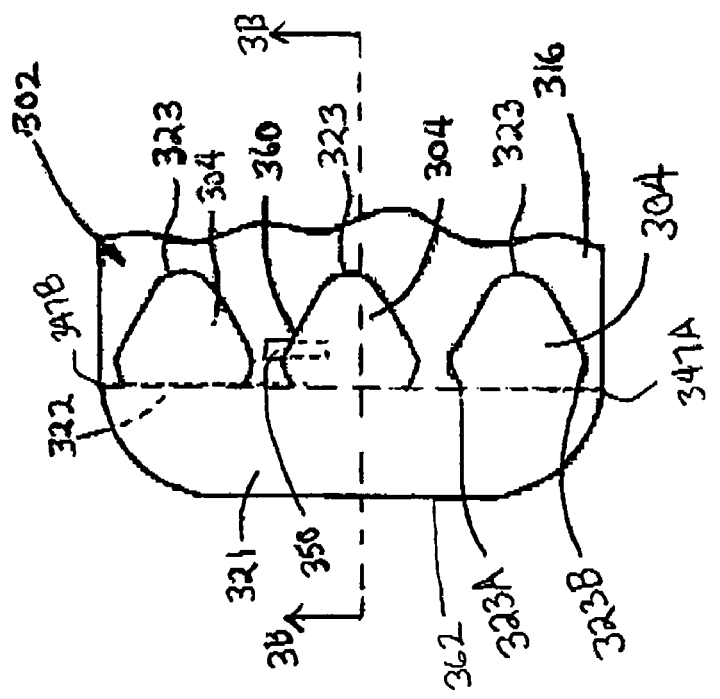
FIG. 3A is a plan view showing an alternative embodiment of a tab member constructed in accordance with the present invention.
Figure 3C:
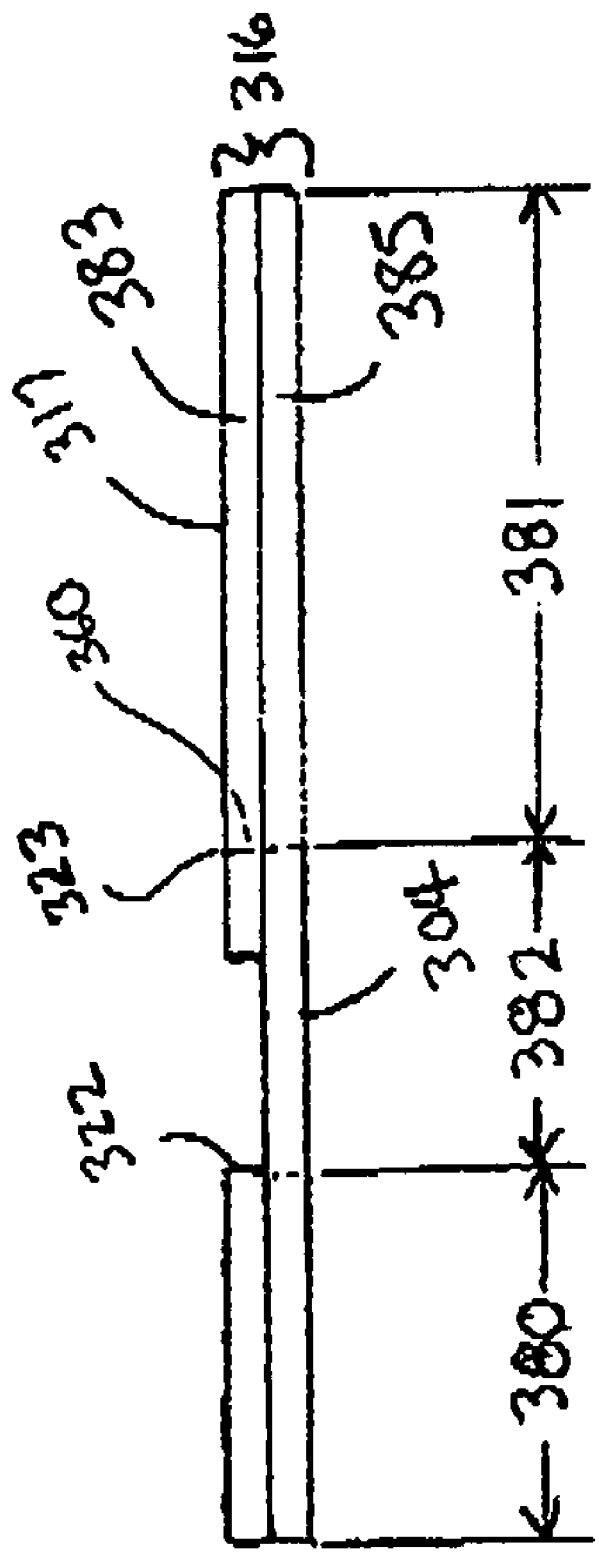
FIG. 3C is a cross sectional view showing another embodiment of a tab member of FIG. 3A.

As shown in FIGS. 3A-3C, alternative to the multiplane hinged tab members discussed above, tab members of the present invention may also be embodied in a single plane hinge tab member. In some embodiments, a single plane hinge tab member can be configured such that no portion of the tab member overhangs another portion of the tab member. Exemplary single plane hinged tab members are described in U.S. Patent Application Publication No. 2003/0233082A1.

As shown in FIG. 3A, a tab member 302 may comprise a substrate element 316 and an anti-pop open device 350. The substrate element 316 further comprises a single plane hinge line 322 and at least one tab element 304. The single plane hinge line 322 for single plane hinged tab members can be similar to the line of attachment 72 (see FIG. 1A). Note as shown, there are three tab elements 304; however, embodiments having fewer than three or more than three are contemplated. In embodiments comprising more than one tab element 304, each tab element 304 may be identically shaped, or alternatively, at least one of the tab elements 304 may be a different shape than another tab element 304. The tab elements 304 can be cut out of the substrate element 316 such that no portions of the tab elements 304 overhang a portion of the substrate element 316.

The tab elements 304 can be formed by cutting a substrate element 316 along at least one cut line 323 to form at least one proximal edge 360. As shown, the cut line 323 can follow a path which begins at a first point 323A and ends at a second point 323B. The path from first point 323A to the second point 323B can form a portion of the single plane hinge line 322. The cut line 323 may take any path provided that the cut line 323 results in at least a portion of the tab element 304 being capable of overlapping an outboard portion of a slot member when the fastening system is engaged. When the tab member 302 is engaged with a slot member, the tab elements 304 may be bent out of the plane of the tab member 302 generally along the single plane hinge line 322 such that tab elements 304 overlap the outboard portion of the slot member. Furthermore, when the tab member 302 is engaged with the slot member, a distal portion 321 of the tab member 302 overlaps an inboard portion of the slot member.

The tab member 302 may further comprise the anti-pop open device 350 which can be disposed between at least one tab element 304 and the substrate element 316 such that a portion of the proximal edge 360 is automatically lifted away from a first surface 317 (see FIG. 3B) of the substrate element 316. As shown, the anti-pop open device 350 can overlap a portion of the substrate element 316 and can be overlapped by a portion of the proximal edge 360 of a tab element 304. In another embodiment, the anti-pop open device 350 can extend from a first longitudinal edge 347A to a second longitudinal edge 347B of the tab member 302. In another embodiment, the anti-pop open device 350 may comprise a plurality of discrete elements which extend from the first longitudinal edge 347A to the second longitudinal edge 347B. Note that for single plane hinged tab members a width of a tab element 304 is the maximum linear distance between a distal edge 362 and the proximal edge 360 in a lateral direction 399.

As shown in FIG. 3B, the cut line 323 may extend from the first surface 317 through a second surface 318 of the substrate element 316 such that the resulting tab elements 304 do not overlap any portion of the substrate element 316. Alternatively, the cut line 323 may extend from the first surface 317 through only a portion of the substrate element 316 such that the resulting tab elements 304 overlap a portion of the substrate element 316.

As shown, the anti-pop open device 350 can be disposed adjacent to the single plane hinge line 322. In another embodiment, the anti-pop open device 350 can be disposed adjacent to the cut line 323. The anti-pop open device 350 can be disposed in any suitable location such that a portion of the proximal edge 360 is lifted away from the first surface 317 of the substrate element 316. The anti-pop open device may comprise any suitable anti-pop open devices discussed herein. For example, at least one tab element 304 may comprise an arcuate component or a beveled component as disclosed for a multi-plane hinged tab member.

As shown in FIG. 3C, in another embodiment, the substrate element 316 may comprise a laminated structure which includes a first layer 383 attached to a second layer 385. The substrate element 316 may further comprise a first region 380, a second region 381, and a weakened region 382 disposed between the first region 380 and the second region 382. The weakened region 382 may comprise a discontinuity in the first layer 383 such that the thickness of the first region 380 and the thickness of the second region 381 are each greater than at least a portion of the thickness of the weakened region 382. As shown, the weakened region 382 can be proximate to the single plane hinge line 322.

The cut line 323 can be positioned on the substrate element 316 such that the tab element 304 comprises a substantial portion of the weakened region 382. Because the single plane hinge line 322 is disposed proximate to the weakened region 382, the reduced thickness of the weakened region 382 can allow a portion of the retaining element 304 to lift away from the surface 317 of the substrate element 316.

The thickness of the weakened region 382 can vary greatly. For example, the thickness of the weakened region 382 can be less than or equal to about 75% of the thicknesses of the first region 380 or the second region 381. As another example, the thickness of the weakened region 382 can be less than or equal to about 50% of the thickness of the first region 381 or the second region 382. As yet another example, the thickness of the weakened region 382 can be less than or equal to about 25% of the thickness of the first region 380 and the second region 381.

In another embodiment, the weakened region 382 can be created by utilizing a substrate element 316 which has a varying basis weight. For example, the basis weight of the first layer 383, the second layer 385, or both, can vary in the weakened region 382 such that there is less material in the weakened region 382 as opposed to the material present in the first region 380 or the second region 381. In yet another embodiment, the basis weight of the first layer 383, the second layer 385, or both, can vary in the first region 380 and the second region 381 such that amount of material available in the first region 380 and the second region 381 is each greater than the material available in the weakened region 382.

In one embodiment, the basis weight of the substrate element 316 in the weakened region 382 can be less than about 25% of the basis weight of the first region 380 or the second region 381. In another embodiment, the basis weight of the weakened region 382 can be less than about 50% of the basis weight of the first region 380 or the second region 381. In yet another embodiment, the basis weight of the weakened region 382 can be less than about 75% of the basis weight of the first region 380 or the second region 381.

The single plane hinged tab member 302, as discussed above, can be a composite including more than one layer of material or may be formed from a single layer of material. Where the tab member 302 includes the first layer 383 and the second layer 385, the first layer 383 or second layer 385 may be a flexible material that would otherwise be insufficiently rigid to perform as a tab member but might provide desirable tactiles or aesthetics. In contrast, the first layer 383 or the second layer 385 can be a more rigid material with suitable stiffness to perform as a tab member and maintain a connection with the slot member under normal loading conditions.

Note that the variation of thickness as discussed above and/or the variation in basis weight of the substrate element 316 is equally applicable to the multiplane hinged tab members discussed heretofore. However, because the tab elements of the multiplane hinged tab members are not cut out from the substrate element, the variation in thickness and/or basis weight can occur in either the substrate element and/or the tab element. For example, the variations in thickness and/or basis weight can occur adjacent to the line of attachment 72 (see FIG. 1).

Regarding FIGS. 4A and 4B, the anti-pop open devices disposed on a tab member, as described herein, cause a portion of a proximal edge of a tab element to lift away from a surface of a substrate element. A relationship between a width of the tab element and the distance by which the portion of the proximal edge of the tab element is displaced from the surface of the substrate element can be established.

As shown in FIG. 4A, a tab member 402 includes a tab element 404 which has a width 498. The width 498 is defined as the distance between a proximal edge 460 and a distal edge 462 of the tab element 404. The width 498 is equal to the maximum linear dimension of the tab element 404 between the proximal edge 460 and the distal edge 462 which is generally parallel to a lateral direction 475.

As shown in FIG. 4B, when disposed on the tab member 402, an anti-pop open device 465 can lift a portion of the proximal edge 460 of the tab element 404 away from a surface 417 of a substrate element 416. The lifting of the proximal edge 460 away from the surface 417 of the substrate element 416 creates a distance 490 between the proximal edge 460 and the surface 417 of the substrate element 416. Note that a method for measuring the distance 490 between the proximal edge 460 and the surface 417 of the substrate element 416 is provided hereafter. In one embodiment, the distance 490 can be greater than about 1% of the width 498 of the tab member 404. In another embodiment, the distance 490 can be greater than or equal to about 10%. In yet another embodiment, the distance 490 can be greater than or equal to about 20%. In yet another embodiment, the distance 490 between the proximal edge 460 and the surface 417 of the substrate element 416 is greater than about 0.5 mm. In yet another embodiment, the distance 490 between the proximal edge 460 and the surface 417 of the substrate element 416 is greater than or equal to about 2.5 mm. In yet another embodiment, the distance 490 between the proximal edge 460 and the surface 417 of the substrate element 416 is greater than or equal to 10 mm.

As stated previously, the anti-pop open device of the present invention may be utilized in either a tab member or a slot member. FIGS. 5A-5H depict various slot members constructed in accordance with the present invention. Any of the slot members discussed herein can be used in conjunction with or independently from the tab members described herein. Other exemplary slots, slot members, tab members, and tab elements, which can be utilized in conjunction with the present invention, are described in U.S. Pat. No. 6,432,098.

As shown in FIGS. 5A-5H, slot members 520 may comprise a slot 546 having an inboard edge 578 and an outboard edge 580. The inboard edge 578 and the outboard edge 580 can define a portion of a slot 546. The slot member 520 may further comprise longitudinal ends 550 which can also define a portion of the slot 546. The slot 546 has a length 504 (denoted as S in FIG. 1A) which corresponds to a distance between the longitudinal ends 550. The slot 546 also has a width 502 which corresponds to a distance between the inboard edge 578 and the outboard edge 580 not including any protrusions.

As shown, the slot members 520 may further comprise an anti-pop open device which may include a protrusion which extends from the inboard edge 578 and/or the outboard edge 580, thereby making the width 502 of the slot 546 non-uniform from one longitudinal edge 550 to the other longitudinal edge 550. For example, as shown in FIG. 5A, a protrusion 582 can extend from the outboard edge 580 into the width 502 of the slot 546 such that the width 502 of the slot 546 is reduced along at least a portion of the length 504 of the slot 546. As shown in FIG. 5B, a plurality of protrusions 582 can extend from the outboard edge 580 into the width 502 of the slot 546. As shown in FIG. 5C, a plurality of protrusions 582 can extend from the outboard edge 580 into the width 502 of the slot 546. In addition, a second plurality of protrusions 581 can extend from the inboard edge 578 into the width 502 of the slot 546. As shown, the protrusions 581 and 582 can have rectilinear surfaces which are rectangular in nature, but they are not limited to such.

As shown in FIGS. 5D-5F, the protrusions 581 and 582 may include various shapes and sizes. For example, as shown in FIG. 5D, the plurality of protrusions 582 which can extend into the width 502 of the slot 546 from the inboard edge 578 may have rounded surfaces which are semicircular in nature. As shown in FIG. 5E, the second plurality of protrusions 581 which can extend from the inboard edge 578 into the width 502 of the slot 546 may also have rounded surfaces which are semicircular in nature. As shown in FIG. 5F, the protrusions 581 and 582 may comprise rectilinear surfaces which are triangular in nature. As shown in FIG. 5G, the protrusion 582 may comprise a rounded surface which gradually bows into the width 502 of the slot 546 over the length 504 of the slot 546. As shown in FIG. 5H, the protrusion 581 may comprise a rounded surface which gradually bows into the width 502 of the slot 546 over the length 504 of the slot 546 either independently from or in conjunction with the protrusion 582.

In one embodiment, a slot member constructed in accordance with the present invention may comprise a plurality of protrusions as described above which have a variety of different surfaces incorporating a variety of shapes. In addition, any shapes and surfaces disclosed herein are merely examples. Any shape known in the art could be utilized to make a width of a slot non-uniform as described above. Furthermore, the shapes protruding from the inboard edge 578 can vary along the inboard edge 578 and can vary from shapes which protrude from the outboard edge 580.

As described above, the slot width 502 may be non-uniform along the length 504 of the slot 546. Any suitable slot width 502 can be used in conjunction with the present invention. In some embodiments, the width 502 of the slot 546 can be in a range from about 0.5 mm to about 6 mm or any individual number within the range. In other embodiments, the width 502 of the slot 546 can be less than about 50% of a width of a tab element. As discussed previously, the width of a tab element is the maximum linear dimension of the tab element between a proximal edge and a distal edge which is generally parallel to a lateral direction (see FIG. 4A). In another embodiment, the width 502 of the slot 546 can be less than or equal to about 25% of the width of the tab element.

Figure 5J:
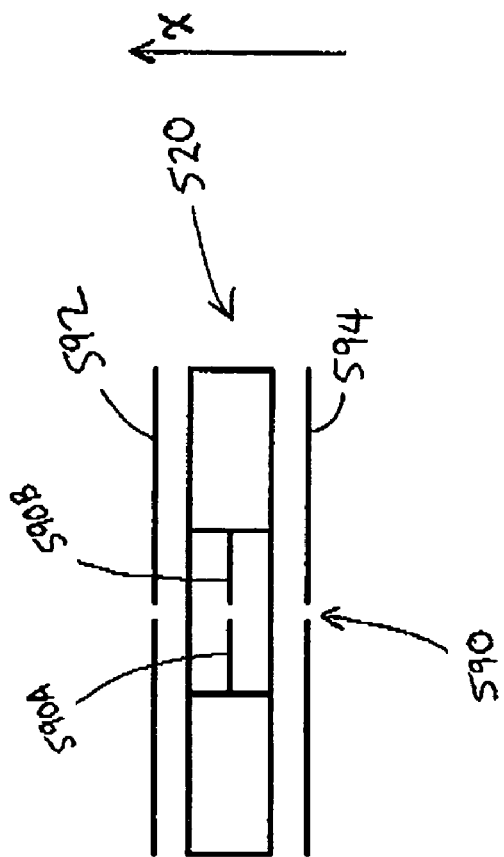
FIG. 5J is an exploded cross sectional view showing the slot member of FIG. 5I as seen through section line 5I-5J.
Figure 5I:
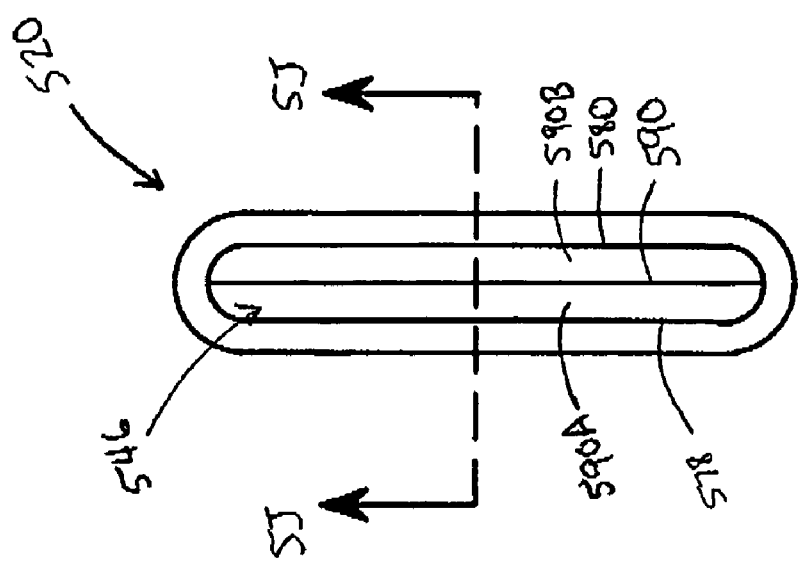

Alternatively, as shown in FIG. 5I, in some embodiments, the slot member 520 can include a slot 546 which further includes a slit 590. A slit is defined as a slot having essentially no gap other than that left by a cutting process, for example. The slit 590 can be defined by a first slit element 590A and a second slit element 590B. Similar to the protrusions described above, the first slit element 590A can extend into the slot 546 from the inboard edge 578 of the slot member 520. Also, the second slit element 590B can extend into the slot 546 from the outboard edge 580.

As shown in FIG. 5J, in some embodiments, the slit may extend through a first nonwoven 592 and through a second nonwoven 594. In some embodiments, a width of the first slit member 590A and/or the second slit member 590B can be greater than 0.0762 mm. In other embodiments, the first slit member 590A and/or the second slit member 590B can have a width which is about equal to a second cross sectional height 675 of the slot member 520. The second cross sectional height is discussed in regard to FIG. 6. In other embodiments, the first slit member 590A and/or the second slit member 590B can have a width which is in a range between 0.0762 mm and the second cross section height 675 or any individual number within the range. The protrusions of FIGS. 5A-5H can have a range of widths similar to the first slot element 590A and/or the second slot element 590B.

Figure 6:
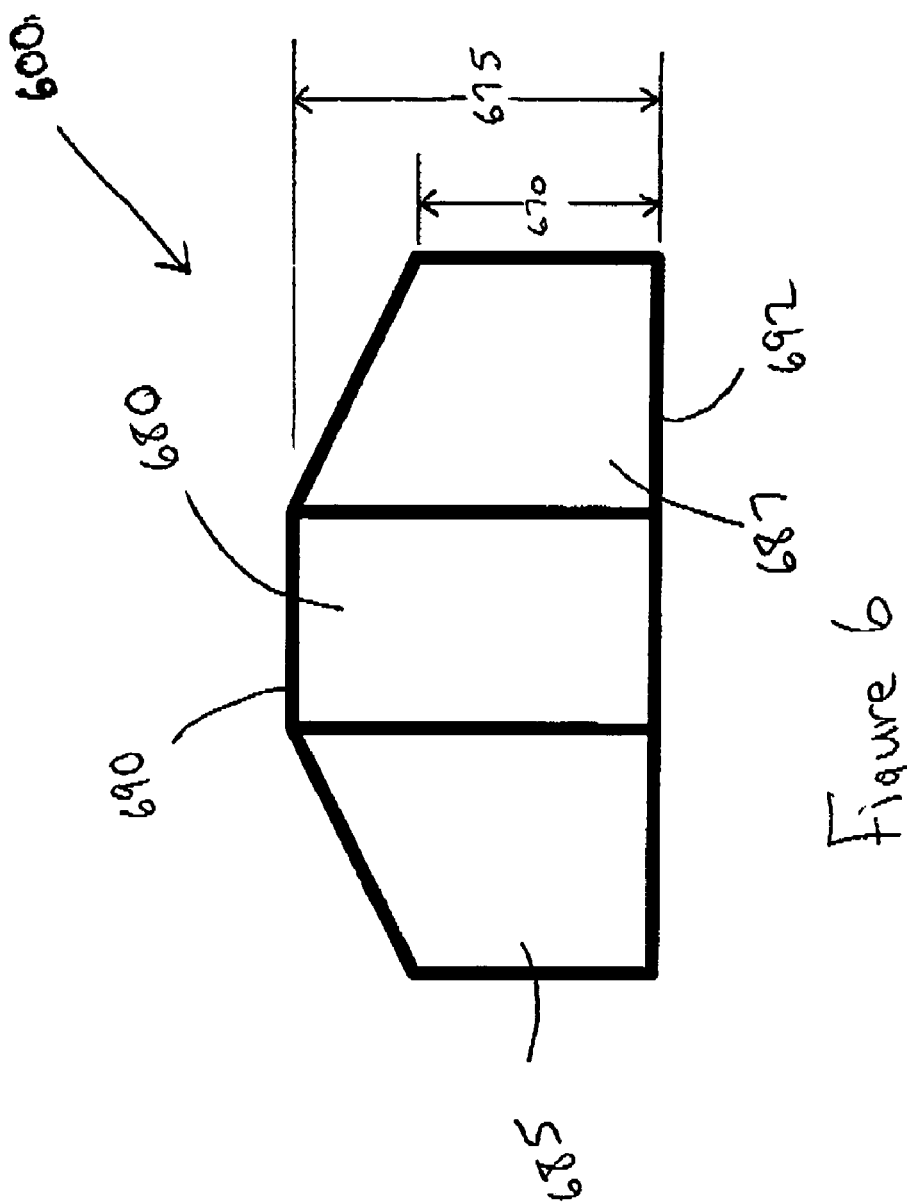
FIG. 6 is an elevation view showing a slot member constructed in accordance with the present invention.

As shown in FIG. 6, a slot member 600 constructed in accordance with the present invention may comprise an inboard portion 685, an outboard portion 687, and a slot 680 between the inboard portion 685 and the outboard portion 687. As shown, an anti-pop open device may comprise a variance in a cross sectional height of the slot member 600 along a lateral direction 699. The slot member 600 may comprise a first cross sectional height 670 adjacent outer edges of the slot member 600. The slot member 600 may further comprise a second cross sectional height 675 which corresponds to the maximum linear distance between a first surface 692 and a second surface 690 of the slot member 600 generally perpendicular to the lateral direction 699. The second cross sectional height 675 can be greater than the first cross sectional height 670.

The difference between the second cross sectional height 675 and the first cross sectional height 670 can be integrally formed into the slot member 600. Alternatively, a separate element may be attached to the slot member such that the second cross sectional height 675 is greater than the first cross sectional height 670.

The second cross sectional height 675 can be greater than the first cross sectional height 670 in only a portion of the slot member 600. In one embodiment, the second cross sectional height 675 can be greater than the first cross sectional height 670 in the outboard portion 687 only. In another embodiment, the second cross sectional height 675 can be greater than the first cross sectional height 670 along a length of the slot 680. In yet another embodiment, a discrete portion, which does not extend along the length of the slot 680, may be attached to the outboard portion 687 such that the second cross sectional height 675 at the location of the discrete portion is greater than the first cross sectional height 670.

The difference in cross sectional heights can cause a portion of a proximal edge of a tab member to automatically lift away from a substrate element, thereby facilitating the engagement of the proximal edge and the outboard portion 687 of the slot member 600 without the caregiver or the wearer having to pivot the tab element. Any suitable difference between the second cross sectional height 675 and the first cross sectional height 670 can be used in the present invention. In one embodiment the first cross sectional height 670 can be at least 0.5 mm while the second cross sectional height 675 can be greater than about 0.5 mm. In another embodiment, the difference between the second cross sectional height 675 and the first cross sectional height 670 can be greater than or equal to about 0.1 mm. In yet another embodiment the difference can be greater than or equal to about 0.25 mm. In yet another embodiment the difference can be greater than or equal to about 0.5 mm.

In addition, a certain ratio of the second cross sectional height 675 to the first cross sectional height 670 may be desired in certain embodiments. For example, in one embodiment, the ratio can be greater than about 1. In another embodiment, the ratio can be greater than or equal to about 1.1. In yet another embodiment, the ratio can be greater than or equal to about 1.25. In yet another embodiment the ratio can be greater than or equal to about 1.5. In yet another embodiment, the ratio can be greater than or equal to about 2.

The tab and slot closure system described herein can be made up of many different materials depending on the use of the closure system. For example, the tab member may be made from any suitable material. Generally, however, the tab member should be sized to fit through the slot of the slot member with little or no bending or deformation of either component. The tab member may be of any size and/or shape. The shape of the tab member will often be dependent on the end use of the tab and slot closure system, but in any case should be aesthetically pleasing, easy to hold and maneuver, and capable of maintaining a fastened configuration throughout the intended period of use when subjected to expected forces and external conditions.

The materials which make up the tab member should also be chosen depending on the end use of the closure system. For example, if the closure system is to be used in a diaper, see FIG. 8, the tab member may include any material suitable for such a use, including but not limited to plastics, films, foams, nonwoven webs, woven webs, paper, laminates, steel, metals, foils, alloys, fiber reinforced plastics and the like, or combinations thereof. In embodiments where the closure system is used near or against the skin of a human or animal, the materials making up the tab member can be flexible. The flexibility allows the closure system to conform to the shape of the body and thus, reduces the likelihood that the closure system will irritate or injure the wearer's skin.

The tab member may include one or more tab elements. Similarly, one or more tab elements may include an anti-pop open device. If the tab member includes more than one tab element, the tab elements are preferably operatively associated with each other such that they generally function as a single tab element. Because an embodiment wherein the tab element comprises a plurality of tab elements generally functions as a single tab member, the complexity of the closure system is reduced and it ensures that a single fastening motion can engage the tab member including a plurality of tab elements. The use of a plurality of tab elements in a tab member is discussed in U.S. Pat. No. 6,432,098.

The tab element may be unitary with the substrate element or may be a separate element attached thereto. The tab element may be attached to the substrate element at any location. Where the tab element is separately attached to the substrate element, the tab element may be made of the same or different materials than substrate element, making it easy to match the exact properties of the closure system to the intended use. Further, the material from which the tab element is made can be reinforced and/or weakened at certain locations to help provide the desired flexibility and stiffness to the closure system. In one embodiment the tab element may be reinforced and/or weakened at one or both of its longitudinal ends 47 (see FIG. 1A). In another embodiment, the tab element may include a grip tab which may be reinforced and/or weakened. Methods of weakening the material of the tab element include scoring, cutting, thinning, bending, heat treating, chemical treating and the like. Methods of reinforcing include heat or chemical treating the material, adding material, increasing the thickness and the like.

The tab member may also include a secondary fastening member which provides a different means for fastening the components of the closure system to each other. For example, the tab member may include secondary fastening member located adjacent the distal edge of the tab element or adjacent a grip portion. The secondary fastening member can be used to provide the closure system with the ability to better resist shear or peel forces, greater adjustability or other properties.

Further, the secondary fastening member may provide the user with a means for fastening the article in a disposal configuration. The secondary fastening member can be any fastening means such as hooks, loops, adhesive, cohesive, magnetic materials, static electricity, snaps and the like or any combination of these or other known fastening means.

Tab members constructed in accordance with the present invention can be made in many different manners. Depending on the material selection of the tab element, a number of different processes by which the proximal edge can be lifted away from a surface of the substrate element may exist. For example, if the tab element comprises a pliable material which can retain its shape, the tab element may be folded or bent such that the proximal edge is lifted away from the surface of the substrate element.

Figure 7:
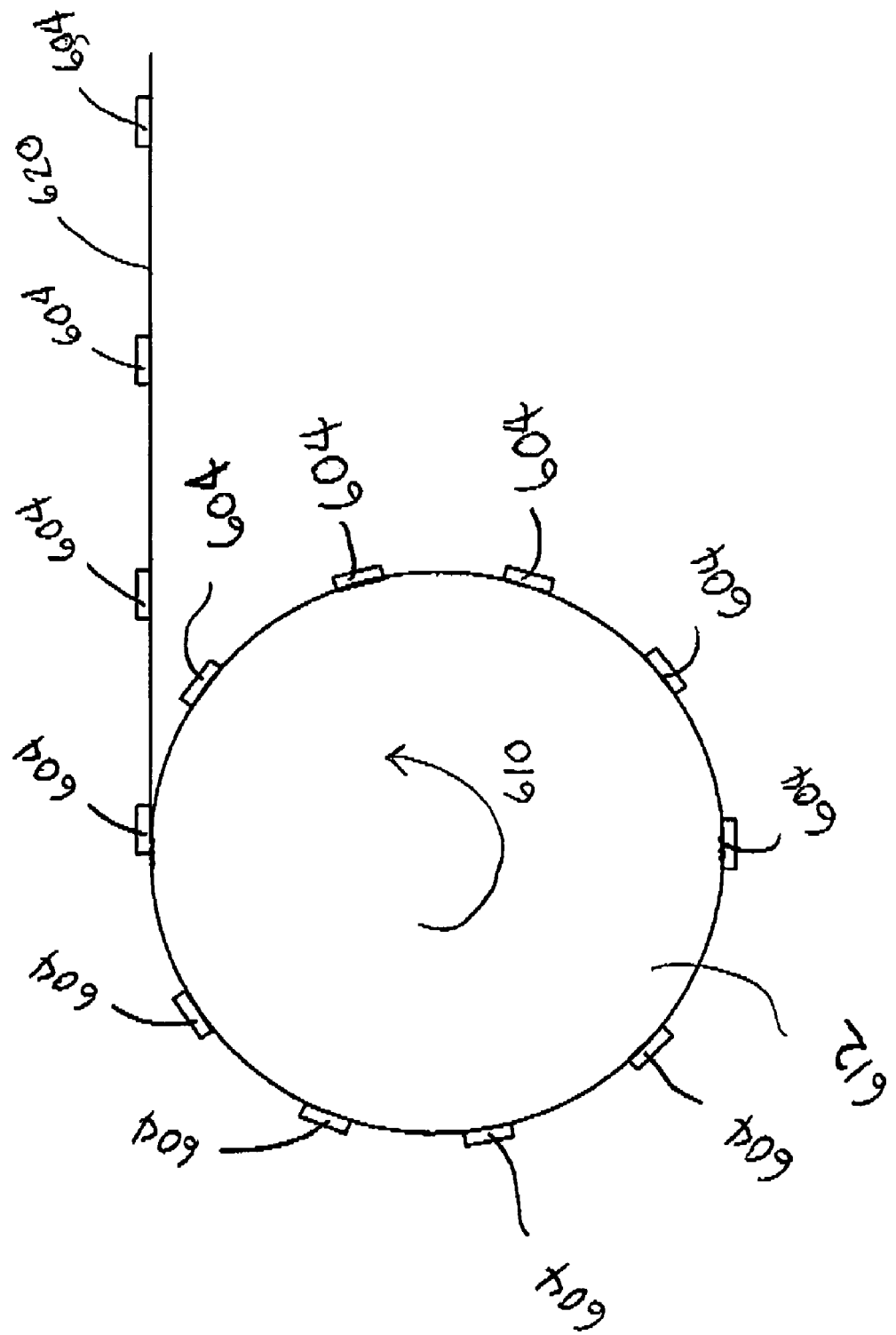
FIG. 7 is a schematic showing a winding process which can be utilized to create tab members in accordance with the present invention.

As shown in FIG. 7, a wind direction 610 can also achieve the creation of tab members in accordance with the present invention. As shown, a tab member can be created on a continuous web 620. Typically, after the tab members are created, they are roll wound and subsequently cut into individual tab members. As shown, tab elements 604 can be placed on the continuous web 620 at spaced apart locations. It has been found, where the tab elements 604 comprise a polypropylene component, that winding the tab elements 604 in the wind direction 610, such that the tab elements 604 face the exterior of the roll 612, can cause the tab elements 604 of the individual tab members to bow. It has also been found that the bowing of the tab elements 604 can cause a proximal edge of the tab element 604 to be lifted away from a surface of the continuous web 620 when unwound. Note that this method may work for any material which can experience permanent set while in a wound state.

Another method for producing multiplane hinged tab members in accordance with the present invention involves an unequal strain process. For example, a tab element can be attached to a substrate element while the substrate element is under tension. If the tab element is not under the same tension as the substrate element, once the substrate element and the tab element are relaxed, the tab element may bow. It has been found that the tab element can bow such that a proximal edge of the tab element is lifted away from a surface of the substrate element. Any suitable strain difference between the substrate element and the tab element can be applied to achieve the objective of the present invention. For example, a strain of between about 10% to about 20% in the substrate element, above the strain of the tab element, can be sufficient to cause the tab element to bow, thereby lifting away a portion of the proximal edge of the tab element. Note that the embodiments discussed herein are not relegated to assembly via an unequal strain process.

As discussed previously, the tab and slot closure system described herein can be made up of many different materials depending on the use of the closure system. Similar to the tab member, the slot member may be of any size and/or shape and may be made from any suitable material. As with the tab member, the shape of the slot member and the materials which make up the slot member will be dependent on the end use of the closure system. For example, in end uses such as diapers, the slot member should be designed to be skin friendly, i.e. not harmful to the wearer's skin. Thus, it may be desirable to round the edges of the closure system and to size the slot(s) so as to minimize the likelihood that skin will be caught in the closure system. One way of minimizing the risk is to work the edges of the slot such that they are not sharp. Another way to make the closure system more skin friendly includes minimizing the thickness of the slot member (e.g. less than about 0.05 inches) or to design the tab member or slot member such that the slot is filled in when the fastening device is closed. One more way is to provide a soft or compressible material on at least the surface of the closure system which faces the wearer.

The slot member may be made of materials the same as or different from the tab member including plastics, films, foams, nonwoven webs, woven webs, paper, laminates, steel, fiber reinforced plastics and the like, or combinations thereof. As with the tab member, the materials making up the slot member may be flexible. However, the slot member should be stiff enough in a lateral direction so as not to deform and let the tab member disengage under normal in use fastening forces. The material from which the slot member is made can be reinforced or weakened at certain locations to help provide the desired flexibility and stiffness to the fastening device. In one embodiment the slot member may be reinforced and/or weakened at one or both of its longitudinal ends.

The slot member may also include a secondary fastening member which provides a different means for fastening the components of the closure system to each other. For example, the slot member may include secondary fastening member located adjacent the inboard portion, the outboard portion, a grip portion, or any other portion of the slot member. As noted with regard to the tab member, the secondary fastening member can be used to provide the closure system with the ability to better resist shear or peel forces, greater adjustability, a disposal feature and/or other features. The secondary fastening member can be any known fastening means such as those described hereinbefore and may function together with or independently of any secondary fastening member disposed on the tab member.

Slot members constructed in accordance with the present invention can be made in many different manners. Depending on the material selection of the slot member, a number of different processes by which the slot member reduces the likelihood that the tab member will prematurely disengage the slot member may exist. For example, if the slot member comprises a material which is able to be machined, the inboard and outboard portions of the slot member may be machined such that protrusions which extend into the width of the slot are created thereon. Alternatively, or in conjunction with the protrusions, the cross sectional height difference previously discussed may also be machined on a second surface of the slot member. For materials which are not necessarily amenable to machining, separate elements may be added to the inboard and outboard portions thereby making protrusions which extend into the slot.

Figure 8:
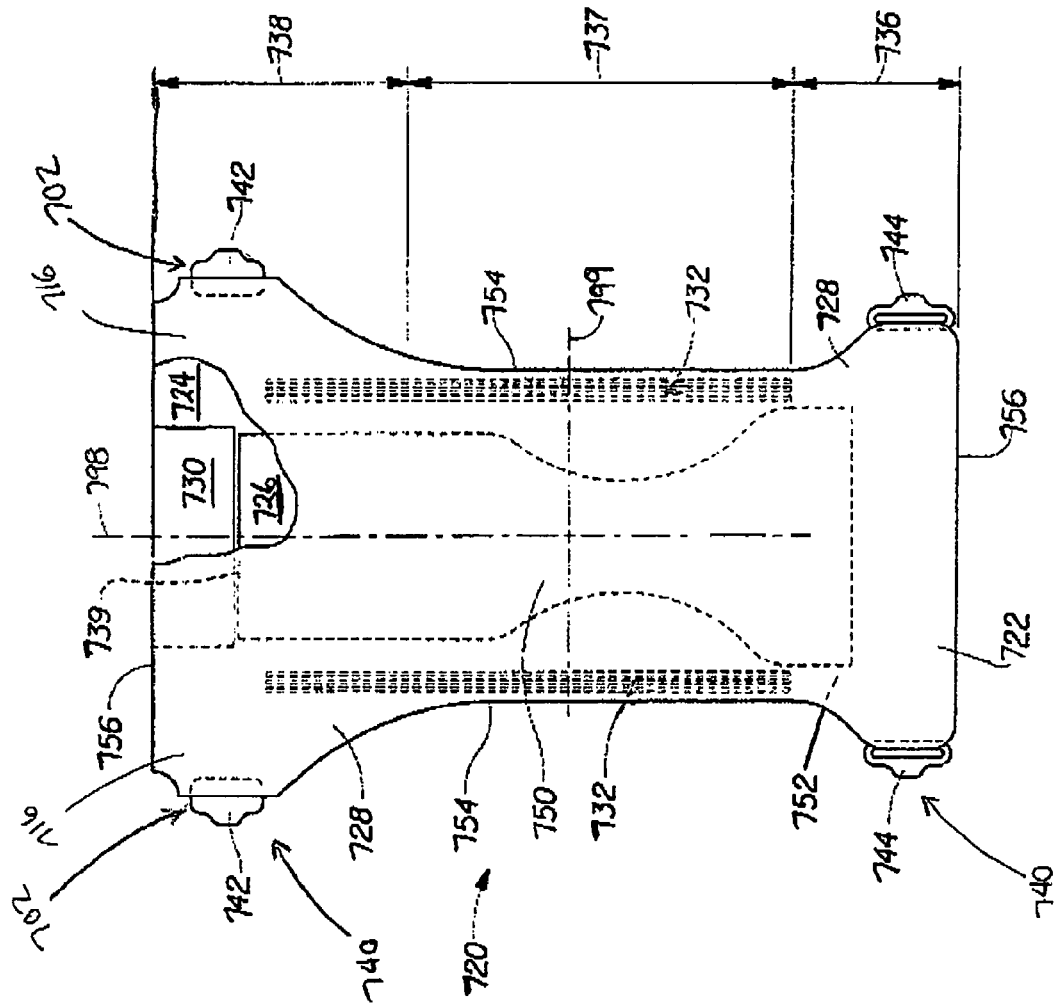
FIG. 8 is a partial cut-away view showing a disposable absorbent article constructed in accordance with the present invention, the disposable absorbent article is shown in a flat, uncontracted state (i.e., without elastic induced contraction).

Uses of the Tab and Slot Closure System:

As shown FIG. 8, a tab and slot closure system constructed in accordance with the present invention can be utilized in a disposable absorbent article such as a diaper 720. As shown, the diaper 720 is in its flat-out, uncontracted state (i.e., with elastic induced contraction pulled out) with portions of the structure being cut-away to more clearly show the construction of the diaper 720. The portion of the diaper 720 which faces or contacts the wearer, the inner surface 750, is oriented towards the viewer. The diaper 720 may comprise a liquid pervious topsheet 722 and a backsheet 724 attached to at least a portion of the topsheet 722. The diaper 720 further comprises an absorbent core 726 positioned between the topsheet 722 and the backsheet 724. The diaper 720 may further comprise side panels 728, leg cuffs 732, and a waist feature 730.

The diaper 720 is shown in FIG. 8 to have an outer surface 752 opposed to the inner surface 750, a first waist region 736, a second waist region 738 opposed to the first waist region 736, a crotch region 737 positioned between the first waist region 736 and the second waist region 738. The diaper 720 also has longitudinal edges 754 and end edges 756. The longitudinal edges 754 run generally parallel to a longitudinal centerline 798, and the end edge 756 run generally parallel to a lateral centerline 799.

The waist feature 730 can help provide improved fit and containment of the diaper 720 about a wearer. The waist feature 730 is that portion or zone of the diaper 720 which is intended to elastically expand and contract to dynamically fit the wearer's waist. The elastic waist feature 730 generally extends longitudinally outward from at least one of the waist edges 739 of the absorbent core 726 and generally forms at least a portion of the end edge 756 of the diaper 720. The elastic waist feature 730 or any of its constituent elements can include a separate element affixed to the diaper 720, the elastic waist feature 730 can be constructed as an extension of other elements of the diaper 720 such as the backsheet 724, the topsheet 722 or both the backsheet 724 and the topsheet 722. Examples of suitable waist features include those described in U.S. Pat. Nos. 4,515,595, 5,151,092, and 5,221,274. Although disposable diapers are generally constructed so as to have two elastic waist features, one positioned in a first waist region and one positioned in a second waist region, diapers can be constructed with a single elastic waist feature as shown in FIG. 8.

The diaper 720 further comprises a fastening system 740 which joins at least a portion of the first waist region 736 with at least a portion of the second waist region 738, preferably to form leg and waist openings. The fastening system 740 also works with the waist feature(s) 730 to maintain lateral tension in order to keep the diaper 720 in place about the waist of the wearer. The fastening system 740 may be the primary fastening system for joining the first and second waist regions 736 and 738. However, the fastening system 740 may be used alone or in conjunction with other fastening means such as hook and loop fasteners, tape fasteners, snaps, buttons, and the like to provide different fastening characteristics. For example, the fastening system 740 may provide the diaper 720 with a disposal means for fastening the diaper 720 in a configuration convenient for disposal. Further, secondary fastening means may provide the diaper 720 with a means for adjusting fit or may increase the strength of the connection between the first waist region 736 and the second waist region 738. The fastening system 740 may comprise a tab member 702 and a slot member 744.

Either the tab member 702 or the slot member 744 may comprise an anti-pop open device as described herein. For example, the tab member 702 may comprise an anti-pop open device which prevents a tab element 742 from prematurely passing back through the slot member 744 once the fastening system 740 has been fastened.

As shown, a substrate element 716 can be integral with the diaper 720. Alternatively, the substrate element 716 can be an element separately attached to the chassis 740 in the second waist region 738. Alternatively, the substrate elements 716 can be attached to the chassis 740 in the first waist region 736. The substrate elements 716 can be elastically extensible such that in the tab members 702 can extend and contract, thereby providing a comfortable fit to a wearer.

The slot member 744 may be unitary with the article to which it is attached or may be a separate element joined thereto. Further, the slot member 744 may be joined to the article at any suitable location. As shown, the slot member 744 is disposed in the first waist region 736. In a disposable absorbent article embodiment, the slot member 744 may be an extension of the material making up the side panel or any other portion of the diaper 720. Alternatively, the slot member 744 may be a separate element which is joined to the article. In any such case, the slot member 744 may be made of the same or different materials than the article to which it is attached.

Note that the fastening system 740 can be prefastened such that a caregiver or wearer may pull on the diaper 720 when removed from a package. Alternatively, the fastening system 740 can be unfastened in the package such that the caregiver or wearer fastens the fastening system while donning the diaper 720. In yet another embodiment, a package may comprise both prefastened and unfastened diapers 720 for the convenience of the caregiver or the wearer. In yet another embodiment, a portion of the fastening system 740 can be prefastened such that the wearer or caregiver fastens the remaining portion of the fastening system 740 to don the article on the wearer.

The topsheet 722 and the backsheet 724 can have length and width dimensions generally larger than those of the absorbent core 726. The topsheet 722 and the backsheet 724 can extend beyond the edges of the absorbent core 726, thereby forming the periphery of the diaper 720. The topsheet 722, the backsheet 724, and the absorbent core 726 may include many different materials and may be assembled in a variety of well known configurations, exemplary diaper materials and configurations are described generally in U.S. Pat. Nos. 3,860,003, 5,151,092, and 5,221,274.

Some examples of suitable topsheets are described further in U.S. Pat. Nos. 3,929,135; 4,324,246; 4,342,314; 4,463,045; 5,006,394; 4,609,518; 4,629,643. Any portion of the topsheet may be coated with a lotion as is known in the art. Examples of suitable lotions include those described in U.S. Pat. Nos. 5,607,760; 5,609,587; 5,635,191; 5,643,588; 5,968,025; 6,716,441; and PCT Publication No. WO 95/24173. Further, the topsheet may be fully or partially elasticated or may be foreshortened so as to provide a void space between the topsheet and the absorbent core. Exemplary structures including elasticized or foreshortened topsheets are described in more detail in U.S. Pat. Nos. 4,892,536; 4,990,147; 5,037,416; and 5,269,775.

A suitable backsheet for use in the disposable absorbent article of the present invention may be impervious to liquids (e.g., urine) and comprise a thin plastic film such as a thermoplastic film having a thickness, for example, of about 0.012 mm (0.5 mil) to about 0.051 mm (2.0 mils). Suitable backsheet films include those manufactured by Tredegar Corporation, based in Richmond, Va., and sold under the trade name CPC2 film. Other suitable backsheet materials may include breathable materials which permit vapors to escape from the pull-on garment while still preventing exudates from passing through the backsheet. Suitable breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va. and sold under the designation EXAIRE, and monolithic films such as manufactured by Clopay Corporation, Cincinnati, Ohio under the name HYTREL blend P18-3097. Some breathable composite materials are described in greater detail in PCT Application No. WO 95/16746; U.S. Pat. Nos. 5,938,648; 5,865,823; and 5,571,096.

The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518, 801. In alternate embodiments, the backsheet may comprise elastic films, foams, strands, or combinations of these or other suitable materials with nonwovens or synthetic films.

A suitable absorbent core for use in the present invention may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure (s) may have varying caliper zones, hydrophilic gradient(s), a superabsorbent gradient(s), or lower average density and lower average basis weight acquisition zones; or may comprise one or more layers or structures). Suitable absorbent structures for use as the absorbent core are described in U.S. Pat. Nos. 4,610,678; 4,673,402; 4,834,735; 4,888,231; 5,137, 537; 5,147,345; 5,342,338; 5,260,345; 5,387,207; and 5,625, 222.

The backsheet may be attached to the topsheet, the absorbent core, or any other element of the disposable absorbent article by any attachment means known in the art. For example, the attachment means may include a uniform continuous layer of adhesive, a patterned layer of adhesive, or an array of separate lines, spirals, or spots of adhesive. Some suitable attachment means are disclosed in U.S. Pat. Nos. 4,573,986; 3,911,173; 4,785,996; and 4,842,666. Examples of suitable adhesives are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Various sublayers may be disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the pull-on garment or may be one or more separate elements attached directly or indirectly with one or more elements of the disposable absorbent article. Further, the sublayer may include a structure that is separate from the absorbent core or may include or be part of at least a portion of the absorbent core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials which are capable of transporting fluids by capillary action. The term "macroporous" refers to materials having pores too large to effect capillary transport of fluid, generally having pores greater than about 0.5 mm in diameter and, more specifically, having pores greater than about 1.0 mm in diameter.) One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga.

Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Embodiments of the present invention may include acquisition layers and dusting layers, each of which are well known in the art. Acquisition layer are further discussed in U.S. Pat. No. 5,460,622. Dusting layers are further discussed in U.S. Pat. No. 4,888,231.

The diaper 720 preferably further comprises leg cuffs 732 to improve containment of liquids and other body exudates. Each elasticized leg cuff may include several different embodiments for reducing the leakage of body exudates in the leg regions. (The leg cuff can also be referred to as leg bands, side flaps, barrier cuffs, or elastic cuffs.) U.S. Pat. No. 3,860, 003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff 732.

Embodiments of the present invention may also include pockets for receiving and containing waste, spacers which provide voids for waste, barriers for limiting the movement of waste in the article, compartments or voids which accept and contain waste materials deposited in the pull-on garment, and the like, or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids in an absorbent article are disclosed in U.S. Pat. Nos. 4,968,312; 4,990,147; 5,062,840; and 5,269,755. Examples of suitable transverse barriers are described in U.S. Pat. No. 5,554,142; PCT Patent WO 94/14395; and U.S. Pat. No. 5,653,703. Examples of other structures suitable for management of low viscosity feces are disclosed in U.S. Pat. Nos. 5,941,864; 5,977,430; and 6,013,063.

The tab and slot closure system of the present invention can be utilized in a number of different absorbent or non-absorbent articles. For example, the tab and slot closure system of the present invention can be utilized in catamenial products, bibs, or wraps as described in U.S. Pat. No. 6,432,098.

Test Methods:

All measures to be carried out in temperature and humidity controlled conditions. Temperature is to be 22° C.+/−2° C. Relative Humidity is to be 50%+/−10%. All samples are to be held at these conditions for 24 hours prior to testing to allow them to equilibrate to the conditions.

Where the tab and slot closure system are utilized in a disposable absorbent article, enough representative absorbent articles are selected from the retail packaging of the absorbent article to conduct all required tests. Tab members and slot members are removed from the disposable absorbent article by cutting via a pair of scissors.

Tab Width Method

1. Position the tab element on a flat, level surface. There should be no external forces on the tab element other than the force of gravity. The tab element should not be compressed, bent, deflected or changed from its natural, relaxed state.

2. Measure the maximum linear distance from a distal edge to a proximal edge that is parallel to a lateral direction. Measurement is to be made to the nearest 0.25 mm. Any measurement device that is calibrated to measure accurately & precisely to 0.25 mm may be used, such as a standard metric (SI) ruler that is graduated in millimeters, a set of calipers, or an image analysis technique.

Cross Sectional Height Difference of a Slot Member

The cross sectional heights of the slot member are to be measured to the nearest 0.05 mm at an applied pressure which does not cause deformation of greater than 0.005 mm of the sample while being measured. Use a measuring device such as a Vernier caliper or micrometer that is calibrated to measure to the nearest 0.05 mm without causing deformation of the sample and is capable of measuring small areas. For example, to measure thickness near an edge of the slot (or within regions of the tab member), the head of the measuring device may need to have a diameter of ~1 mm or smaller.

1. Measure cross sectional height of the slot member adjacent the slot (within 0.5 mm of slot 680). If the cross sectional height is not uniform adjacent to the slot, then the maximum cross sectional height between a first surface and a second surface of the slot member should be measured adjacent to the slot. Record the measurement as "second cross sectional height".
2. Measure the cross sectional height of the slot member adjacent the outer edges of the slot member (within 0.5 mm of slot member's perimeter defining the outer edges). If the cross sectional height is not uniform adjacent the outer edges of the slot member, then the minimum cross sectional height between the first surface and the second surface of the slot member is measured adjacent to the outer edges. Record the measurement as the "first cross sectional height".
3. Compare the thickness of the first cross-sectional height to that of the second cross-sectional height. Calculations follow:
   a. Difference in cross sectional heights=(second cross-sectional height)−(first cross-sectional height).
   b. Ratio of cross-sectional heights=(second cross-sectional height)/(first cross-sectional height).

Thickness Difference in Substrate Element and/or Tab element

The cross sectional heights of the substrate element and/or the tab element are to be measured to the nearest 0.05 mm at an applied pressure which does not cause deformation of greater than 0.005 mm of the sample while being measured. Use a measuring device such as a Vernier caliper or micrometer that is calibrated to measure to the nearest 0.05 mm without causing deformation of the sample and is capable of measuring small areas.

1. Measure thickness of a first region, a second region, and a weakened region. The measurement includes all layers of the substrate element.
Calculations follow:

Ratio of thicknesses, expressed as %=100*(thickness of weakened region)/(thickness of first region)
OR Ratio of thicknesses, expressed as %=100*(thickness of weakened region)/(thickness of second region).

Method to Measure Basis Weight Variation
Basis Weight is mass per unit area and is to be measured in grams per square meter, to the nearest 1 gram/m².
1. Basis weight is to be measured using any suitable method of determining mass per unit area. Suitable methods include EDANA 40.3-90. Smaller test areas may be used if needed to measure basis weight variations within the test sample (substrate element and/or tab element). In any case, a sample of known area is weighed. The result is determined by dividing the mass of the sample by the area of the sample. The fastening device should be measured sufficiently to determine basis weight variations in a lateral direction and a longitudinal direction of a test sample.
2. Calculations follow:

Ratio of Basis Weights, expressed as %=100*(Basis Weight of weakened region)/(Basis Weight of first region).

Ratio of Basis Weights, expressed as %=100*(Basis Weight of weakened region)/(Basis Weight of second region).

Method to Measure Height of Proximal Edge from Substrate Element

Figure 9A:
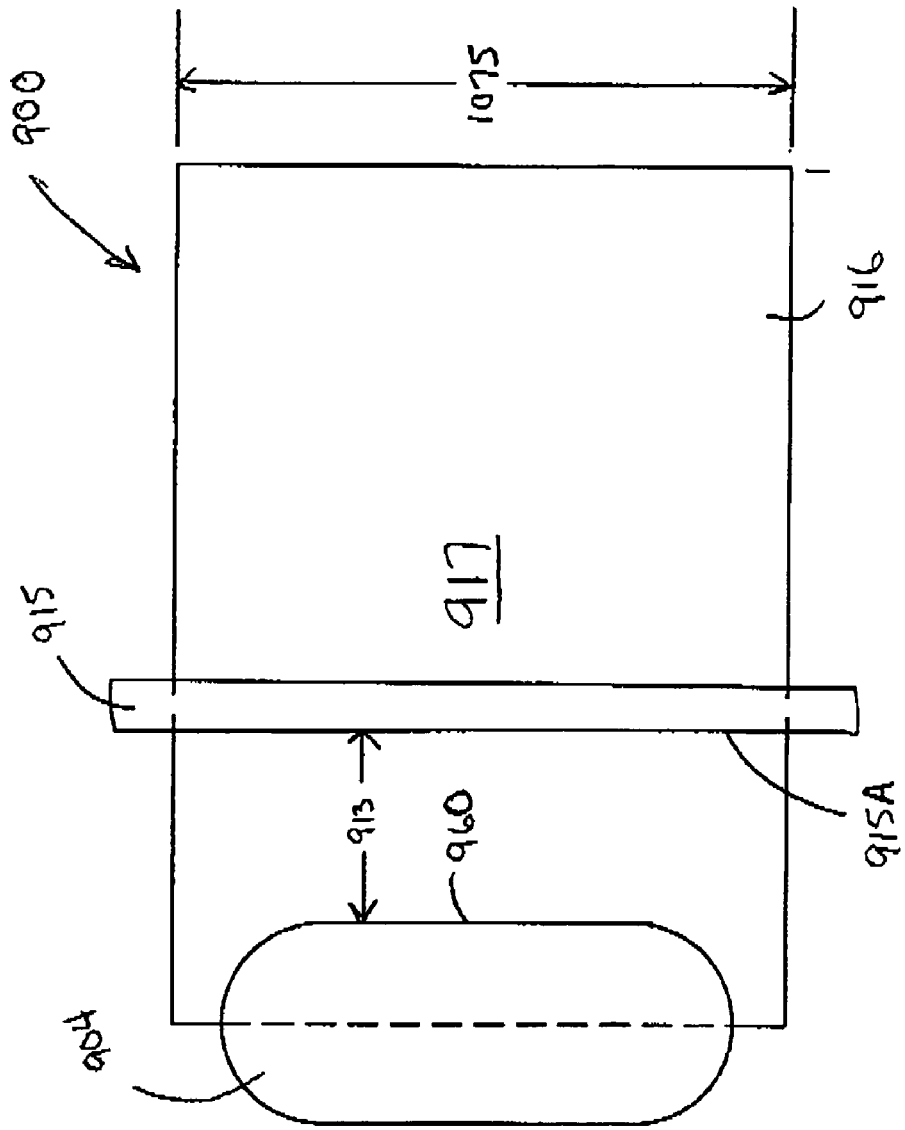
FIG. 9A is a plan view of a tab member on a flat horizontal surface.
Figure 9B:
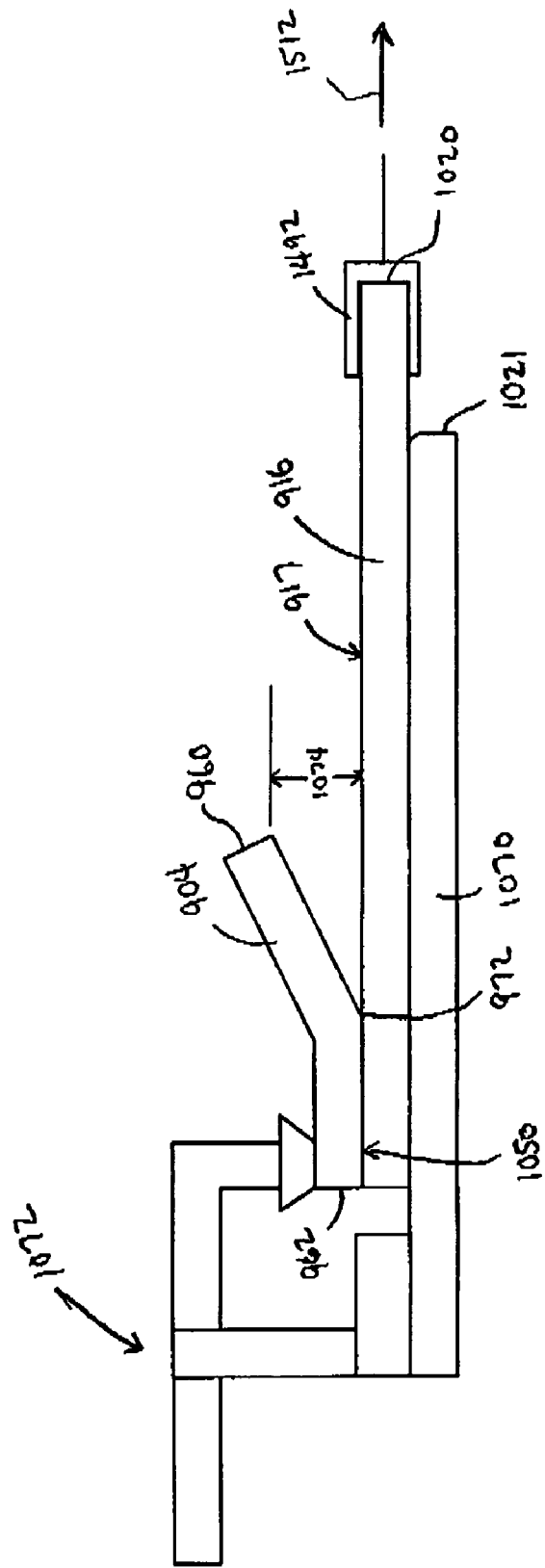
FIG. 9B is an elevation view of the tab member of FIG. 9A, wherein the tab member is in an extended state.

1. As shown in FIG. 9A, obtain a completed tab member 900, i.e. a tab element 904 attached to a substrate element 916.
2. Lay the tab member 900 on a flat horizontal surface 1070 (see FIG. 9B) such that tab element 904 is facing upwards and such that the entire tab member 900 is disposed on the flat horizontal surface 1070 (see FIG. 9B).
3. Affix a holding device 915 to the flat horizontal surface 1070 such that the holding device 915 applies a pressure of 6.89 kPa (1 psi) to the substrate element 916. The holding device 915 applies the pressure evenly across a width 1075 of the substrate element 916. A leading edge 915A of the holding device 915 is placed at a distance 913 which is 10 mm from the proximal edge 960 of the tab element 904.
4. Measure a distance 1074 (see FIG. 9B) from an intersection of a proximal edge 960 and a bottom surface 1050 (see FIG. 9B) of the tab element 904 to a surface 917 of the substrate element 916. Although not shown, the measurement for single plane hinged tab members should be performed in the same manner. Distance is measured to the nearest 0.5 mm using any suitably calibrated equipment, such as a standard metric (SI) ruler, calipers, or image analysis techniques. The measurement direction is to be within 0.5 degrees of vertical.
5. Record the measurement as a first measurement.
6. Remove holding device 915 from the flat horizontal surface 1070.
7. As shown in FIG. 9B, clamp the tab element 904 to the flat horizontal surface 1070 such that the bottom surface 1050 of the tab element 904 adjacent a distal edge 962 is in contact with the flat horizontal surface 1070 and such that an end 1020 of the substrate element 916 extends over an edge 1021 of the flat horizontal surface 1070. The clamp 1072 is fastened to the tab element 904 and the flat horizontal surface 1070 such that the clamp 1072 does not extend beyond 50% of a distance between the distal edge 962 and a line of attachment 972. The bottom surface 1050 adjacent to the distal edge 962 is clamped to the flat surface via a clamp model no. 225-U manufactured by De-Sta-Co. or equivalent.
8. Affix a clamp 1492 adjacent to the end 1020 of the substrate element 916. The clamp 1492 is affixed to the substrate element 916 such that the clamp can distribute an applied force evenly across the width 1075 of the substrate element 916.

9. Apply a force of 0.075 to 0.125 Newtons/cm of width 1075 of the substrate element 916 to the clamp 1492. The force is measured with a calibrated force gauge such as an Accuforce Cadet™ force gauge made by Ametek, Mansfield & Green Division. The force is applied in a direction which is within 0.5 degrees of a plane of the flat horizontal surface 1070. Note that the flat horizontal surface 1070 is smooth such that the substrate element 916 may move with respect to the flat horizontal surface 1070 without engaging any asperities on the flat horizontal surface 1070.

10. Measure the distance 1074 from an intersection of the proximal edge 960 and a bottom surface of the tab element 904 to a surface 917 of the substrate element 916. Although not shown, the measurement for single plane hinged tab members is performed in the same manner. Distance is measured to the nearest 0.5 mm using any suitably calibrated equipment, such as a standard metric (SI) ruler, calipers, or image analysis techniques. The measurement direction is to be within 0.5 degrees of vertical.

11. Record measurement as second measurement.

12. Compare the first measurement and the second measurement. Discard the smaller of the two measurements.

End of Test Methods.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tab and slot closure system comprising:
   a) a tab member including:
      i) a tab element including an outer surface and an inner surface, and a first region having a proximal edge, a second region having a distal edge, and a line of attachment disposed between the proximal edge and the distal edge; and
      ii) a substrate element attached to the inner surface of the tab element along the line of attachment,
   b) a slot member having an outer surface and an inner surface, an inboard portion and an outboard portion, and a slot disposed between the inboard portion and the outboard portion, wherein when the closure system is fastened a portion of the substrate element extends into the slot member to the line of attachment, and at least a portion of the inner surface of the first region of the tab element overlaps the outer surface of the outboard portion of the slot member; and
   c) an anti-pop open device disposed on the tab member or the slot member, wherein the anti-pop open device includes a beveled component disposed in the first region, wherein the anti-pop open device causes at least a portion of the proximal edge of the tab element to lift away from the substrate element, thereby reducing the likelihood of the tab element unintentionally passing back through the slot.

2. The tab and slot closure system of claim 1, wherein the tab element further comprises a length, and wherein the line of attachment extends to about at least 25% of the length of the tab member.

3. The tab and slot closure system of claim 1, wherein the anti-pop open device is disposed on the tab member.

4. The tab and slot closure system of claim 3, wherein the anti-pop open device comprises a beveled component disposed in the first region such that a portion of the proximal edge is lifted away from a surface of the substrate element.

5. The tab and slot closure system of claim 3, wherein the anti-pop open device comprises an arcuate component disposed in the first region such that a portion of the proximal edge is lifted away from a surface of the substrate element.

6. The tab and slot closure system of claim 5, wherein the second region comprises an arcuate component such that the distal edge is displaced away from the surface of the substrate element.

7. The tab and slot closure system of claim 3, wherein the anti-pop open device comprises a spacing element disposed adjacent to the line of attachment, and wherein a first portion of the spacing element is disposed on the substrate element and a second portion is disposed on the tab element.

8. The tab and slot closure system of claim 3, wherein the anti-pop open device comprises a spacing element disposed between the substrate element and the tab element.

9. The tab and slot closure system of claim 8, wherein the spacing element is attached to the substrate element and attached to the second region of the tab element.

10. The tab and slot closure system of claim 8, wherein the spacing element is disposed between the substrate element and the first region of the tab member such that the proximal edge is lifted away from a surface of the substrate element.

11. The tab and slot closure system of claim 10, wherein the spacing element is attached to the substrate element and unattached to the tab element.

12. The tab and slot closure system of claim 3, wherein the tab element comprises a width defined by the proximal edge and the distal edge, and wherein the anti-pop open device creates a distance between the proximal edge and the substrate element which is greater than about 5% of the width of the tab element.

13. The tab and slot closure system of claim 1, wherein the anti-pop open device is disposed on the slot member.

14. The tab and slot closure system of claim 13, wherein the inboard portion and the outboard portion define a width of the slot, and wherein the anti-pop open device creates a non-uniform slot width along a length of the slot.

15. The tab and slot closure system of claim 14, wherein the anti-pop open device comprises at least one protrusion extending into the width of the slot from the inboard portion or the outboard portion, thereby causing a non-uniform width in the slot.

16. The tab and slot closure system of claim 15, wherein the at least one protrusion extends from the outboard portion into the width of the slot.

17. The tab and slot closure system of claim 15, wherein the anti-pop open device comprises at least one protrusion extending from the inboard portion and at least one protrusion extending from the outboard portion.

18. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; the disposable absorbent article further comprising:

a topsheet;

a backsheet attached to at least a portion of the topsheet; and an absorbent core disposed between the topsheet and the backsheet;

a tab and slot closure system comprising:

a) a tab member comprising:

i) a tab element including an outer surface and an inner surface, and a first region having a proximal edge, a second region having a distal edge, and a line of attachment disposed between the proximal edge and the distal edge; and ii) a substrate element attached to the inner surface of the tab element along the line of attachment, wherein the substrate element is attached to the disposable absorbent article in the second waist region;

b) a slot member including an outer surface and an inner surface, an inboard portion and an outboard portion, and a slot disposed between the inboard portion and the outboard portion, wherein the slot member is disposed in the first waist region of the disposable absorbent article, and wherein when the closure system is fastened, a portion of the substrate element extends into the slot member to the line of attachment, and the at least a portion of the inner surface of the proximal edge of the tab element overlaps the outer surface of the outboard portion of the slot member; and c) an anti-pop open device disposed on the tab member, wherein the anti-pop open device includes a beveled component disposed in the first region wherein the anti-pop open device causes at least a portion of the proximal edge of the tab element to lift away from the substrate element, thereby reducing the likelihood of the tab element unintentionally passing back through the slot.

19. The disposable absorbent article of claim 18, wherein the portion of the proximal edge is lifted away from a surface of the substrate element by a distance which is greater than or equal to about 1% of a width of the tab element.

20. A package of disposable absorbent articles comprising a plurality of disposable absorbent articles for wearing about the lower torso of a wearer, wherein at least one of the disposable absorbent articles comprises: a first waist region, a second waist region, a crotch region disposed between the first and second waist regions; a first waist edge and a second waist edge; and a first longitudinal edge and a second longitudinal edge; the at least one of the disposable absorbent articles further comprising:

a topsheet;

a backsheet attached to at least a portion of the topsheet; and an absorbent core disposed between the topsheet and the backsheet;

a tab and slot closure system comprising:

a) a tab member comprising:

i) a tab element including an outer surface and an inner surface, and including a first region having a proximal edge, a second region having a distal edge, and a line of attachment disposed between the proximal edge and the distal edge; and ii) a substrate element attached to the inner surface of the tab element along the line of attachment, wherein the substrate element is attached to the disposable absorbent article in the second waist region;

b) a slot member including an outer surface and an inner surface, an inboard portion and an outboard portion, and a slot disposed between the inboard portion and the outboard portion, wherein the slot member is disposed in the first waist region of the disposable absorbent article, and wherein when the closure system is fastened a portion of the substrate element extends into the slot member to the line of attachment, and at least a portion of the inner surface of the proximal edge of the tab element overlaps the outer surface of the outboard portion of the slot member, wherein the tab and slot closure system is prefastened; and c) an anti-pop open device disposed on the tab member or the slot member, wherein the anti-pop open device includes a beveled component disposed in the first region, wherein the anti-pop open device causes at least a portion of the proximal edge of the tab element to lift away from the substrate element, thereby reducing the likelihood of the tab element unintentionally passing back through the slot.

\* \* \* \* \*